(12) United States Patent
Nagasawa et al.

(10) Patent No.: US 6,355,775 B1
(45) Date of Patent: Mar. 12, 2002

(54) TRANSCRIPTIONAL INHIBITOR

(75) Inventors: Yasuo Nagasawa; Hideaki Yoshida, both of Tokyo (JP)

(73) Assignee: Institute Of Cytosignal Research, Inc., Tokyo (JP)

( * ) Notice: Subject to any disclaimer, the term of this patent is extended or adjusted under 35 U.S.C. 154(b) by 0 days.

(21) Appl. No.: 09/308,160

(22) PCT Filed: Nov. 12, 1997

(86) PCT No.: PCT/JP97/04127

§ 371 Date: Jun. 16, 1999

§ 102(e) Date: Jun. 16, 1999

(87) PCT Pub. No.: WO98/22581

PCT Pub. Date: May 28, 1998

(30) Foreign Application Priority Data

Nov. 15, 1996 (JP) .............................................. 8-305043

(51) Int. Cl.[7] .................................................. C07K 1/00
(52) U.S. Cl. ........................ 530/350; 530/350; 530/300; 530/387.3; 435/7.1; 435/6; 435/69.7; 435/325; 435/320.1; 424/143.1; 424/93.21; 536/23.5
(58) Field of Search .............................. 530/350, 387.3, 530/300; 435/69.7, 6, 320.1, 7.1, 325; 424/143.1, 93.21; 536/23.5

(56) References Cited

PUBLICATIONS

Sheridan et al., (Alignment: Accession No: Q14527), 1995.*
Unger et al., The Plant Cell, vol. 5, pp. 831–841, Aug. 1993.
Brown et al., Oncogene, vol. 8, pp. 877–886, 1993.
Moriggl et al., Molecular and Cellular Biology, vol. 16, No. 10, pp. 5691–5700, Oct. 1996.
Zhu et al., Development, vol. 122, pp. 1577–1587, 1996.
Xing et al., Biochemistry, vol. 34, pp. 3956–3963, 1995.
Ding et al., DNA and Cell Biology, vol. 15, No. 6, pp. 429–442, 1996.
Sheridan et al., The Journal of Biological Chemistry, vol. 270, No. 9, pp. 4575–4587, Mar. 1995.
Gong et al., Development Biology, vol. 183, pp. 166–182, 1997.
Hayward–Lester et al., Molecular Endocrinology, vol. 10, No. 11, pp. 1335–1349, 1996.

* cited by examiner

Primary Examiner—Karen Cochrane Carlson
Assistant Examiner—Hope A. Robinson
(74) Attorney, Agent, or Firm—Shanks & Herbert

(57) ABSTRACT

A protein having transcription inhibitory activity and lacking at least a part of regions other than a region having DNA binding activity in a transcriptional regulatory factor is provided. This protein can be obtained by isolating cDNA encoding a protein capable of binding to the transcriptional regulatory region of the gene transcription of which is to be inhibited, deleting from the cDNA at least a part of the regions other than the region having DNA-binding activity, inserting the resulting DNA into an appropriate vector, introducing said vector into cells to allow them to express the deleted gene, and isolating and purifying a protein showing the transcription inhibitory activity. For example, the protein can be used in the field of pharmaceuticals as a therapeutic agent. Its use in the field of gene therapy is also expected.

6 Claims, 23 Drawing Sheets primer SR1: 5'– ATGAGCTCAGAACCAGCTGTGGAATG
                        SacI
primer SR2: 5'– CTGTTCTGCGCCCGTTACAAAACCAGAAAGTTAACTG
primer SR3: 5'– TTACTTCTGCTCTAAAAGCTGGCGCGCCCCTGCAGT
primer SR4: 5'– TCACCTAAATCGTATGTGCCAGACATGATAAGATACAT
primer SR5: 5'– CAGTTAACTTTCTGGTTTTGTAACGGGCGCAGAACAG
primer SR6: 5'– ACTGCAGGGGCGCCAGCTTTTAGAGCAGAAGTAA
primer SR7: 5'– ATGTATCTTATCATGTCTGGCACATACGATTTAGGTGA
primer SR8: 5'– TAGGTACCGTCGACCCCTGAACCTGAAACATAAAA
                        KpnI

FIG.2

```
        10         20         30         40         50         60
GGCGGCCCT GCAGTCTAGA GAATTCCCAC GAATCAAATG GCCCGGGCCA GAAGATGCAT
                                           ‾‾‾‾‾‾‾‾‾‾‾‾‾‾‾‾‾‾‾‾
                                  CTTAGTTTAC CGGGCCCGGT CTTCTACGTA
                                  ‾‾‾‾‾‾‾‾‾‾‾‾‾‾‾‾‾‾‾‾‾‾‾‾‾‾‾‾‾‾
        70         80         90        100        110
GGCTCGAGGC GGCCGCAAGC TTCTATAG
∼∼∼∼∼∼∼∼∼∼∼∼∼∼∼∼∼∼∼∼∼∼∼∼∼∼∼∼
CCGAGCTCCG CCGGCGTTCG AAGATATCAC AGTGGATTTA GCATACAC
========== ========== ========== ========== ‾‾‾‾‾‾‾‾
```

MCS-1: DNA sequence represented by ———
MCS-2: DNA sequence represented by ∼∼∼
MCS-3: DNA sequence represented by ===
MCS-4: DNA sequence represented by ———

FIG.3

SRO-1: 5'— ATGAGCTCAGAACCAGCTGTGGAATG —3'

SRO-2: 5'— CCGAGGCAAGCTTGGCCTCGGCCCTCTGCATAAA —3'

SRO-3: 5'— CGAGGCCAAGCTTGCCTCGGCCCTCTGAGCTATT —3'

SRO-4: 5'— ATGGTACCGGCCCGGCGTAACGGCGCAGAACAGAAAA —3'

FIG.6

SacI
ATGAGCTCAGAACCAGCTGTGGAATGTGTGTCAGTTAGGGTGTGTGGAAAGTCCCCAGGCTCCCCAGCAGGCAGAAGT
ATGCAAAGCATGCATCTCAATTAGTCAGCAACCAGGTGTGGAAAGTCCCCAGGCTCCCCAGCAGGCAGAAGTATGC
AAAGCATGCATCTCAATTAGTCAGCAACCATAGTCCCGCCCCTAACTCCGCCCCATCCGCCCCTAACTCCGCCCAG
                                                        HindIII
TTCCGCCCCATTCTCCGCCCCATGGCTGACTAATTTTTTTATTTTATGCAGAGGCCGAGGCCAAGCTTGCCTCGGCC
TCTGAGCTATTCCAGAAGTAGTGAGGAGGCTTTTTTGGAGGCCTAGGCTTTGGGCTCGATCTCTCCTTCACGCGC
CCGCCGCCCCTACCTGAGGCCCATCCACGCCGGTTGCTGAGTCGCCGCCTCCCCGTGTGCCTCCTGA
ACTCGTCCGCCGTCTAGGTAAGTTTAAAGCTCAGGTCGAGACCCGGCCTTTGTCGCGGCTCCCCTTGGAGCCTAC
CTAGACTCAGCGCCGGCTCTCCACGCTTTGCCTGACCCCTGCTCAACTCTAGTCTTTGTTTCTGTTCT
     NotI    Asp718I
GCGCCCGTTACGGCGGCCGCGGGTACCAT

FIG.7

PRIMER 1   5'-TCGCGATTCCCACGAATCAAATGGC-3' (WITH THE Nru I SITE AT 5' END)
PRIMER 2   5'-TCTGGCACATACGATTTAGGT

TRANSCRIPTIONAL INHIBITOR

This application is a 371 of PCT/JP97/04127, filed Nov. 12, 1997 and claims foreign priority to Ser. No. 8/305,043, filed Nov. 15, 1996.

TECHNICAL FIELD

The present invention relates to the field of genetic engineering. For example, the protein of the present invention can be used in the field of pharmaceuticals as a therapeutic agent.

BACKGROUND ART

A gene is transcribed by forming a transcription initiation complex including RNA polymerase bound to the promoter region upstream to the gene. Gene transcription is considered to be regulated mainly by transcriptional regulatory factors binding to the promoter and interactive with the transcription initiation complex. In general, a transcriptional regulatory factor comprises a DNA binding region and a transcriptional activation region. The transcriptional activation region is considered to be involved in the interaction.

The relation between the expression of specific genes and various diseases has been revealed in the field of medical treatment. For example, the expression of cytokine genes, such as TNF (Molecular Medicine 33: 1010–1020 (1996)), IL-1 (Clin. Immunol. 27: 18–28 (1995)), and IL-8 (Clin. Immunol. 27: 80–85 (1995)), are reported to be associated with various diseases, including inflammation. Hyperactivated transcription of IL-2 is involved in the immune diseases such as graft rejection.

Furthermore, diseases for which there is currently no effective treatment, such as virus infections including cancer and AIDS, can be controlled if expression of a responsible cancer gene (such as c-Myc) and virus gene is inhibited.

Such diseases can be treated if the transcriptional regulatory factor involved in the disease is isolated and its function is controlled. Therefore, transcriptional regulatory factors drew much attention as targets for developing new drugs.

An inhibitor of a transcriptional regulatory factor has been screened by a DNA binding inhibitory experiment in a chemical library or natural substances derived from bacteria or plants, or by drug design based on the structure of a gene or a transcriptional factor to becontrolled (Peterson, M. G. et al., Trends Biotechnol. 11: 11–18 (1993).

The DNA binding inhibitory experiment requires screening numerous samples. However, there is no effective method of screening at present.

Furthermore, drug design requires that the structure of transcriptional regulatory factors must be known in detail. Therefore, its application is limited.

DISCLOSURE OF THE INVENTION

An objective of the present invention is to provide a protein having transcription-inhibitory activity, more specifically, a protein having transcription-inhibitory activity on a specific promoter.

Normal animal cells contain hypoxanthine-guanine phosphoribosyl-transferase (HGPRT), thus, uptake 6-thioguanine (6-TG) in their nucleic acid synthetic pathway. Those cells die in a 6-TG-containing medium due to its toxicity. In contrast, HGPRT-deficient mutant cells survive and proliferate in the 6-TG-containing medium, unaffected by the toxicity because those cells do not uptake 6-thioguanine (6-TG) in the nucleic acid synthetic pathway. Therefore, in the HGPRT-deficient mutant cells, the survival of the cells in the presence of 6-thioguanine (6-TG) can be determined by controlling the expression of HGPRT (or a protein with a similar function). The present inventors constructed the system to search for a gene involved in intracellular signal transduction, using the above characteristics of the HGPRT-deficient mutant cells.

It is evident that a promoter of the interleukin 8 gene (IL-8) is activated in response to stimulation by a tumor necrosis factor (TNF). The present inventors prepared an expression plasmid carrying a xanthine-guanine phosphoribosyl-transferase (gpt) gene which causes cell death when expressed in the presence of 6-TG similarly to HGPRT, by inserting the gene downstream to the IL-8 promotor sequence in the plasmid vector, and introduced the resultant plasmid into HGPRT-deficient cells. The cells die in the presence of a suitable quantity of 6-TG in response to the TNF stimulation because of the expression of gpt gene. However, when a certain gene capable of inhibiting the signal transduction pathway from the TNF stimulation to the activation of the IL-8 promoter is introduced into the above cells, the expression of gpt can be inhibited and then the cells survive. Therefore, genes capable of inhibiting the intracellular signal transduction can be isolated by introducing various genes in said cells and selecting surviving cells.

The present inventors successfully isolated four genes (S1-15, S1-b2, S2-3, and S20-1) which were suppressive for IL-8 promoter activation from a cDNA library by using the above screening system. The present inventors specifically analyzed "S1-15" which consistently exhibited IL-8 promoter inhibitory activity.

First, the present inventors determined the sequence of "S1-15." Homology searches based on the determined nucleotide sequence found two homologous genes which were reported as those encoding transcriptional regulatory factors.

The present inventors noticed that the transcriptional regulatory factors, which were supposed to enhance transcription inherently, were in fact inhibitory for IL-8 promoter. Then, the present inventors analyzed the amino acid sequence of S1-15 in more detail. They found that S1-15 comprised a DNA binding region within the above transcriptional regulatory factor but lacked most of the rest, including the regions that interact with other factors involved in transcription.

Finally, the present inventors found that the transcriptional regulatory factors can be modified into transcriptional inhibitory factors by deleting sequences other than regions having DNA binding activity of transcriptional regulatory factors, thereby completing the present invention.

Specifically, the present invention relates to:
(1) a protein having transcription inhibitory activity and lacking at least a part of regions other than a region having DNA binding activity in a transcriptional regulatory factor,
(2) the protein of (1), wherein said protein lacks at least a part of the region interacting with other factors involved in transcription in the transcriptional regulatory factor,
(3) a protein having inhibitory activity on transcription of interleukin 8 gene and having the amino acid sequence of SEQ ID NO: 1, or said amino acid sequence in which one or more amino acid residues are substituted, deleted, or added,
(4) a protein having the amino acid sequence of SEQ ID NO: 1, (5) a DNA encoding the protein of (1) to (4),
(6) a vector comprising the DNA of (5),
(7) a cell carrying the vector of (6),
(8) a method of inhibiting transcription of a specific gene, which comprises introducing the protein of (1) or (2) into cells,
(9) a method of inhibiting transcription of the interleukin 8 gene, which comprises introducing the protein of (3) or (4) into cells,
(10) a method of inhibiting transcription of a specific gene, which comprises introducing a vector comprising DNA encoding the protein of (1) or (2) into cells and allowing the protein of (1) or (2) to be expressed in the cells,
(11) a method of inhibiting transcription of the interleukin 8 gene, which comprises introducing a vector comprising DNA encoding the protein of (3) or (4) into cells and allowing the protein of (3) or (4) to to be expressed in the cells.

The term "a transcriptional regulatory factor" used herein means a protein controlling transcription of a gene, other than basal transcription factors. The term "a basal transcription factor" means a factor which forms a transcription initiation complex with RNA polymerase and DNA.

The term "a factor involved in transcription" used herein means a factor regulating gene transcription, including basal transcription factors.

First, the present invention relates to a protein having transcription inhibitory activity and lacking at least a part of the sequences other than those having DNA binding activity of transcriptional regulatory factors.

The protein of the present invention generally includes the region having DNA binding activity of transcriptional regulatory factors. A region having DNA binding activity of transcriptional regulatory factors varies depending on the transcriptional regulatory factor. For example, the bzip (basic-leucine zipper) region in c-JUN (Sutherland, J. A. et al., Genes Dev., 6: 1810–1819(1992)) and Zn finger region in Sp1 (Kadonaga, J. T. et al., Science 242: 1556–1570 (1988). The region having DNA binding activity of transcriptional regulatory factors can vary depending on the upstream region of the gene to be bound. The region having DNA binding activity of transcriptional regulatory factors can be determined by preparing various deletion mutants of transcriptional regulatory factor genes and detecting the DNA binding activity using gel shift assay.

The protein of the present invention also possesses transcription inhibitory activity and lacks at least a part of regions other than those having DNA binding activity. The sequence other than the region having DNA binding activity is not particularly limited as long as deletion of the sequence imparts transcription inhibitory activity. This region preferably interacts with other factors involved in transcription, more preferably, a transcriptional activation region (a region interacting with basal transcription factors). The transcriptional activation region can be determined by replacing amino acid residues by site-specific mutagenesis and detecting the decreased transcription activity by the replacement (Gill, G. et al., Cell 51: 121–126 (1987)).

The protein of the present invention can include not only an amino acid sequence of a part of natural transcriptional factors but also a sequence in which one or more amino acids are deleted, substituted, or added, as long as the protein has the transcription inhibitory activity. Such deletion, substitution, or addition of amino acids can be performed by site-specific mutagenesis well known in the art at the time this application was filed (Nucleic Acid Res., 10: pp. 6487).

The protein can be prepared by the method described below.

First, if a gene's transcription is to be inhibited but the gene encoding the transcriptional regulatory factor is unknown, the gene encoding the transcriptional regulatory factor should be isolated. cDNA encoding the protein capable of binding to the transcriptional regulatory region can be isolated, for example, by screening a cDNA library inserted in a phage vector using the transcriptional regulatory region of a gene whose transcription is to be inhibited as a probe (Vinson, C. R. et al., Genes Dev. 2: 801–806 (1988)).

Second, at least a part of regions other than those having DNA binding activity in the isolated gene encoding the transcriptional regulatory factor are deleted. This deletion is enabled by creating new restriction sites by introducing point mutation in the DNA sequence and utilizing the restriction sites using recombinant DNA technology (commonly used genetic engineering technology such as methods described in "Molecular cloning (Sambrook, J et al., Molecular Cloning; A Laboratory Manual, 2nd ed. Cold Spring Harbor Laboratory, NY (1989)," "Laboratory Manual of Genetic Engineering, Muramatsu, M. ed., Maruzen (1989)") or the "Kunkel method" (Methods Enzymol. 85: 2763–2766 (1988)). The deletion also can be made by PCR (Higuch, R. PCR Protocols, Academic press, INC. 177–183 (1990)).

Third, the obtained DNA is ligated with an appropriate vector, and the vector is introduced into cells to detect transcription inhibitory activity of the expressed protein. The vector to be used is not particularly limited. Preferable examples of the vector include "pcDL-SR α 296" comprising SR α promoter capable of effectively expressing the gene to be expressed (Takebe, Y. et al., Mol. Cell. Biol. 8: 466–472 (1988)), "pEF-BOS" comprising the promoter of the elongation factor (Mizushima, S. Nucleic Acid Res. 18 (1990)), or "pCAGGS" comprising CAG (cytomegalovirus IE enhancer+chicken β-globin poly(A) signal) promoter (Niwa, H. et al., GENE 108: 193–200 (1990)).

The cells into which the vector is introduced are not particularly limited. "MRC-5 SV1 TG1 cell" (Riken Cell Bank), "VA-13 cell" (Riken Cell Bank), or "RERF-LC-AI cell" (Riken Cell Bank) is preferable.

The vector can be introduced into the cells by the DEAE-dextran method (Luthman, H. et al., Nucleic Acids Res. 11: 1295–1308 (1983)), the calcium phosphate method (Graham, F. L. et al., Virology 52: 456–457. (1973)), electroporation (Neumann, E. et al., EMBO J. 1: 841–845 (1982), or similar methods.

The transcriptional inhibitory activity can be detected by, for example, reporter assay (Sambrook, J. et al., Molecular Cloning, A Laboratory Manual, 2nd ed., Cold Spring Harbor Laboratory, NY (1989)).

Fourth, the protein whose transcription inhibitory activity was detected is isolated and purified. The isolation and purification can be performed by inserting a gene encoding the protein whose transcription inhibitory activity was detected into an expression vector, transforming prokaryotic or eukaryotic host cells with said vector, and purifying the expressed protein by chromatography or a similar method. For example, when *E. coli* is used as a host, the method of Smith et al. (Smith, D. B. et al., Current Protocols in Molecular Biology Vol. 2, John Wiley & Sons, New York, 16.7. (1990)) can be used.

The protein of the present invention can be prepared by the methods described above.

The present invention also relates to a method of inhibiting transcription of a specific gene using a protein having transcriptional inhibitory activity and lacking at least a part of regions other than those having DNA binding activity of transcriptional regulatory factors.

One embodiment relates to the method of inhibiting transcription of a specific gene and is characterized by introducing said protein into cells.

The cells into which the protein of this invention is to be introduced are not particularly limited. The protein of the present invention can be introduced into cells by microinjection, electroporation, the liposomal method, the erythrocyte ghost method, or some similar method.

Another embodiment relates to a method of inhibiting transcription of a specific gene and is characterized by introducing a vector comprising DNA encoding the protein of the present invention into cells and allowing said protein to be expressed in cells.

Any vector can be used as long as it can express the inserted gene. When animal cells are used, vectors such as "pcDL-SRα296" comprising SRα promoter capable of effectively expressing a gene to be expressed (Takebe, Y. et al., Mol. Cell. Biol. 8: 466–472 (1988)), "pEF-BOS" comprising the promoter of the elongation factor (Mizushima, S. Nucleic Acid Res. 18: (1990)), and "pCAGGS" comprising CAG (cytomegalovirus IE enhancer+chicken β-globin poly (A) signal) promoter (Niwa, H. et al., GENE 108: 193–200 (1990)) are preferable.

The vector can be introduced into cells by the DEAE-dextran method (Luthman, H. et al., NucleicAcids Res. 11: 1295–1308 (1983) ), the calcium phosphate method (Graham, F. L. et al., Virology 52: 456–457. (1973)), electroporation (Neumann, E. et al., EMBO J. 1: 841–845 (1982), or a similar method.

When expression of a gene whose transcription is controlled by the protein of the present invention correlates with a disease, the protein is particularly useful as a therapeutic agent for the disease. For example, if a specific gene is revealed to be an oncogene, the transcriptional regulatory factor based on the sequence upstream of the oncogene is isolated. The transcriptional regulatory factor gene is then isolated to prepare the protein of the present invention. In this case, the protein of the present invention can be used as an anticancer agent. The protein of the present invention can be administered to a patient by subcutaneous injection or other suitable method.

Furthermore, the protein of the present invention can be used to inhibit a disease by expressing it in the patient's body. Transcriptional regulatory factors are believed to bind to the upstream portion of a specific gene with high specificity to the gene. Therefore, the protein of the present invention derived from the transcriptional regulatory factor can also have high specificity to the gene and thus be useful in the field of gene therapy. In this case, the gene encoding the protein of the present invention is inserted into an appropriate vector and can be introduced into the body by, for example, a method using a virus vector or a method using membrane-fused liposomes. The virus vector to be used is not particularly limited. Preferable examples thereof include retrovirus vectors, adenovirus vectors, AAV (adeno-associated virus) vectors, herpesvirus vectors, and HIV vectors.

IL 8 is reported to be produced in various inflammatory diseases, such as chronic articular rheumatism, gouty arthritis, psoriasis, contact dermatitis, sepsis, cataplectic pulmonary fibrosis, adult respiratory distress syndrome, inflammatory enteropathy, immune angiitis, glomerulonephritis, urinary tract infection, myocardinal infarction, respiratory tract infection, asthma, perinatal infection, and rejection to transplanted organs (Matushima, K. et al., Chem Immunol 51: 236–265 (1992)). The protein inhibiting transcription of IL-8 and having the sequence of SEQ ID NO: 1 can be used as a therapeutic agent for the above-described diseases.

BRIEF DESCRIPTION OF THE DRAWINGS

FIG. 2 shows the DNA sequence of the primers (SEQ ID NOS 11–18, respectively) for constructing vector pBlue-SR.

FIG. 3 shows the template DNA sequence of MCS (SEQ ID NOS 19–20, respectively).

FIG. 6 shows the sequence of the synthetic DNA primers (SEQ ID NOS 21–24, respectively) for constructing vetor pBlue-SRα-Hind.

FIG. 7 shows the sequence of the DNA insertion (SEQ ID NOS: 25) into vector pBlue-SRα-Hind.

BEST MODE FOR IMPLEMENTING THE INVENTION

EXAMPLE 1

Figure 1:
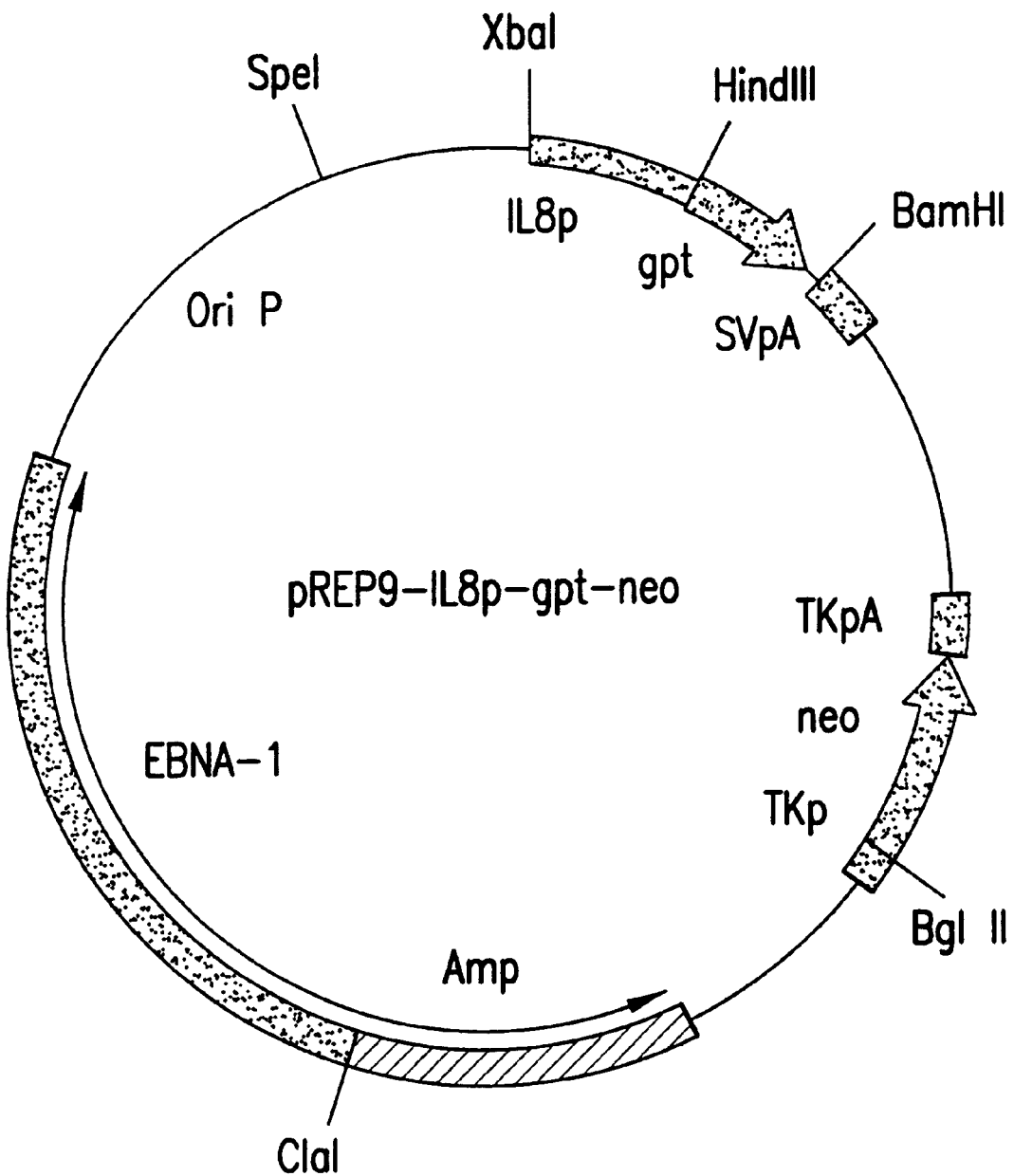
FIG. 1 shows the structure of vector pREP9-IL8p-gpt-neo.

Establishment of the cloning system of a gene relating to inhibition of signal transduction from TNF stimulation to IL-8 promoter activation
1. Construction of Plasmid pREP9-IL8p-gpt-neo (Abbreviated pIL8p-gpt-neo) Having the gpt Gene Downstream of the IL-8 Promoter and the Neomycin Resistance Gene, neo
(1) Construction of pBluescript SK(+)-gpt About 600 bp of the gpt gene region was amplified by PCR using Taq polymerase (TAKARA), the following primers, and pSV2-gpt (Mulligan, R. C. and Berg, P. Science 209, 1422–1427 (1980)) as the template.

Primer #1 (SEQ ID NO: 3) AT AAGCTTTTCACATGAGCGAAAAATACA HindIII

Primer #2 (SEQ ID NO: 4) AT GGATCCCTATTGTAACCCGCCTGAAGT BamHI

PCR was performed with DNA Thermal Cycler Model PJ2000 (TAKARA, PERKIN ELMER CETUS). The reaction mixture contained a PCR buffer (10 mM Tris-HCl, pH 8.3, 50 mM KCl, 1.5 mM $MgCl_2$, 0.001% gelatin), 0.2 mM each (final concentration) of dNTPs (dATP, dCTP, dGTP, dTTP), 1 µM DNA primers, and the template DNA to make the total volume 100 µl. Twenty cycles of incubation at 94° C. for 1 minute, at 50° C. for 1 minute, and at 72° C. for 1 minute were performed. The PCR product was digested with restriction enzymes BamHI and HindIII and purified with the DNA purifying agent preA-gene Matrix (Nippon Bio-Rad Laboratories, BIO-RAD). The fragment was ligated into BamHI- and HindIII-digested pBluescript II SK(+) (TOYOBO, STRATAGENE) with a DNA Ligation Kit (TAKARA) using T4 DNA ligase. Colonies resistant to ampicillin were obtained by introducing the resulting plasmid into the competent cells of XL1-Blue, an E. coli K-12 strain. The plasmids into which the gpt gene was inserted were obtained by collecting plasmids from cultured cells of colonies and examining the restriction pattern. DNA sequencing was performed for the part corresponding to the gpt gene, and the sequence was confirmed to be the desired gpt gene. DNA sequencing was performed with Taq DyeDeoxy™ termination Cycle Sequencing Kit (APPLIED BIOSYSTEMS) along with its protocol. After the reaction, the reaction product was purified with a spin column Bio-Spin 30 (BIO-RAD) and analyzed with a DNA sequencer (ABI 373A DNA Sequencing System).

(2) Construction of pREP-gpt

The BamHI-HindIII fragment (about 600 bp) of pBluescript SK(+)-gpt containing the gpt gene and the BamHI-HindIII fragment (about 10 kb) of pREP9 (FUNAKOSHI, INVITROGEN) were recovered by low-melting point agarose gel electrophoresis and purified with a tip for isolating and purifying nucleic acid, QIAGEN-tip 5 (FUNAKOSHI, QIAGEN Inc.). The two fragments were ligated to each other with DNA Ligation Kit (TAKARA) then introduced into competent cells of E. coli K-12 strain XL1-Blue to obtain colonies resistant to ampicillin. Plasmid DNAs of the transformants were prepared, and clones with the gpt gene were selected. The plasmid thus obtained was named pREP-gpt.

(3) Construction of pREP-IL8-gpt-neo

The human IL-8 promoter region was introduced into pREP-gpt obtained above so that expression of the gpt gene could be regulated. More specifically, DNA fragments containing the human IL-8 (neutrophil chemotactic cytokine) promoter region (Matsushima, K. et al., J. Imm. 143, 1366–1371 (1989)) were prepared by PCR with synthetic primers IL8P1 (5'-ATGTCTCGAGAATTCAGTAACCC-AGGCATTATTTTATC-3' (SEQ ID NO: 5)) and IL8P2 (5'-TTGTCCTAGAAGCTTGTGTGCTCTGCTGTC-3' (SEQ ID NO: 6)), and with a genomic DNA of human VA-13 cells (Riken Cell Bank) as the template. After the fragments were digested with HincII and HindIII, the human IL-8 promoter region (IL8p, −546 to +44) was recovered and purified. pREP-gpt was digested with XbaI, blunted with a DNA Blunting Kit (TAKARA), digested with HindIII, and a 10 kb DNA fragment was purified. The two fragments were ligated with a DNA Ligation Kit (TAKARA) then introduced into the competent cells of JM109 (TOYOBO) to obtain colonies resistant to ampicillin. The plasmid with the structure shown in FIG. 1 was obtained by collecting plasmids from cultured cells of colonies and examining the restriction pattern. In this plasmid, the E. coli gpt gene was ligated to the downstream end (3'-end) of the human IL-8 promoter region (IL8p, −546 to +44), and xanthine-guanine-phosphoribosyltransferase (XGPRT) was thus produced under the control of the human IL-8 promoter. In addition, this plasmid had the neomycin resistance gene, neo, derived from pREP9, as the selection marker.

Figure 4:
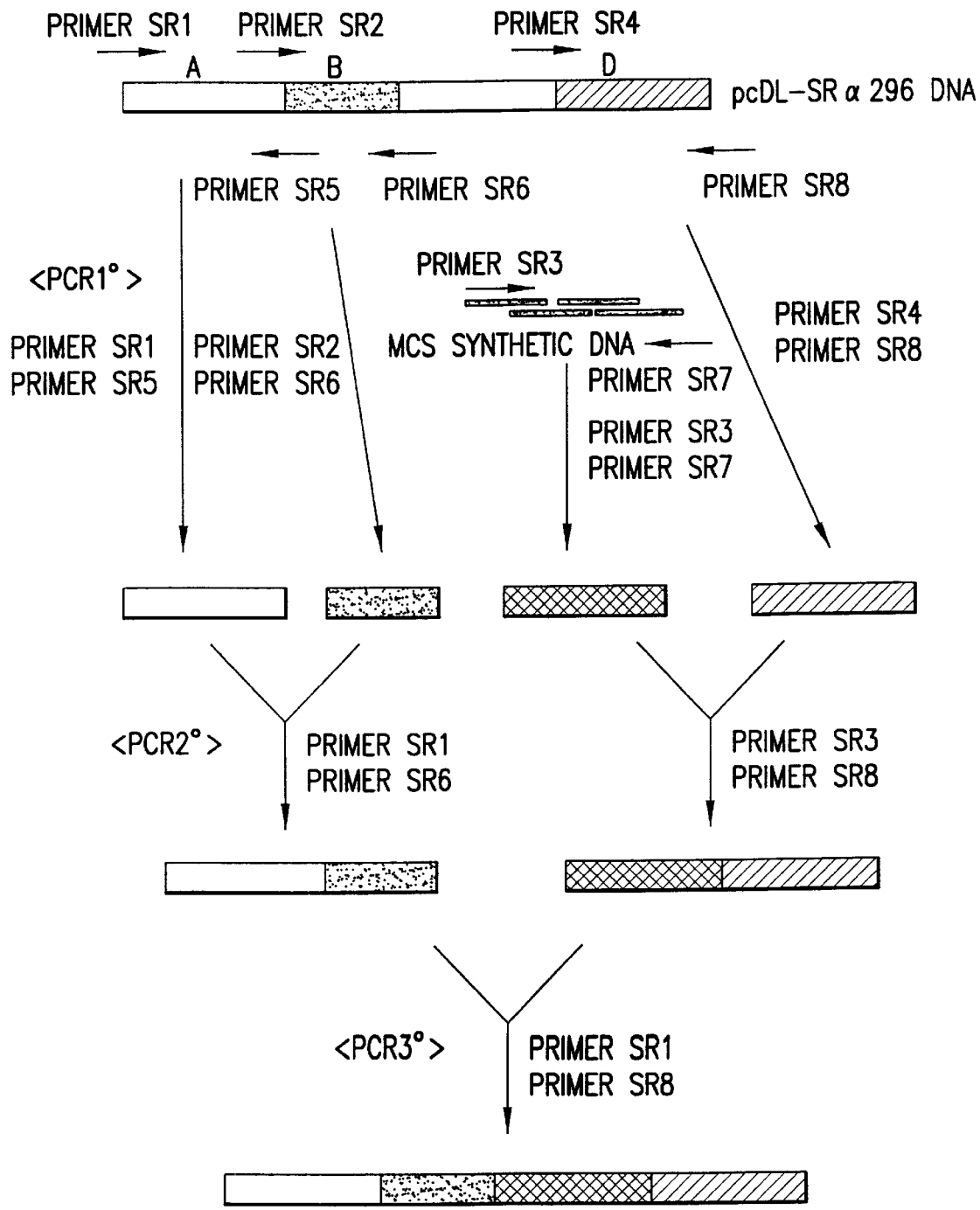
FIG. 4 shows the ligation process of four DNA fragments, SRαpromoter (fragment A), splice site (fragment B), multicloning site (MCS) (fragment C), and polyadenylation signal (fragment D), for constructing vector pBlue-SR.
Figure 5:
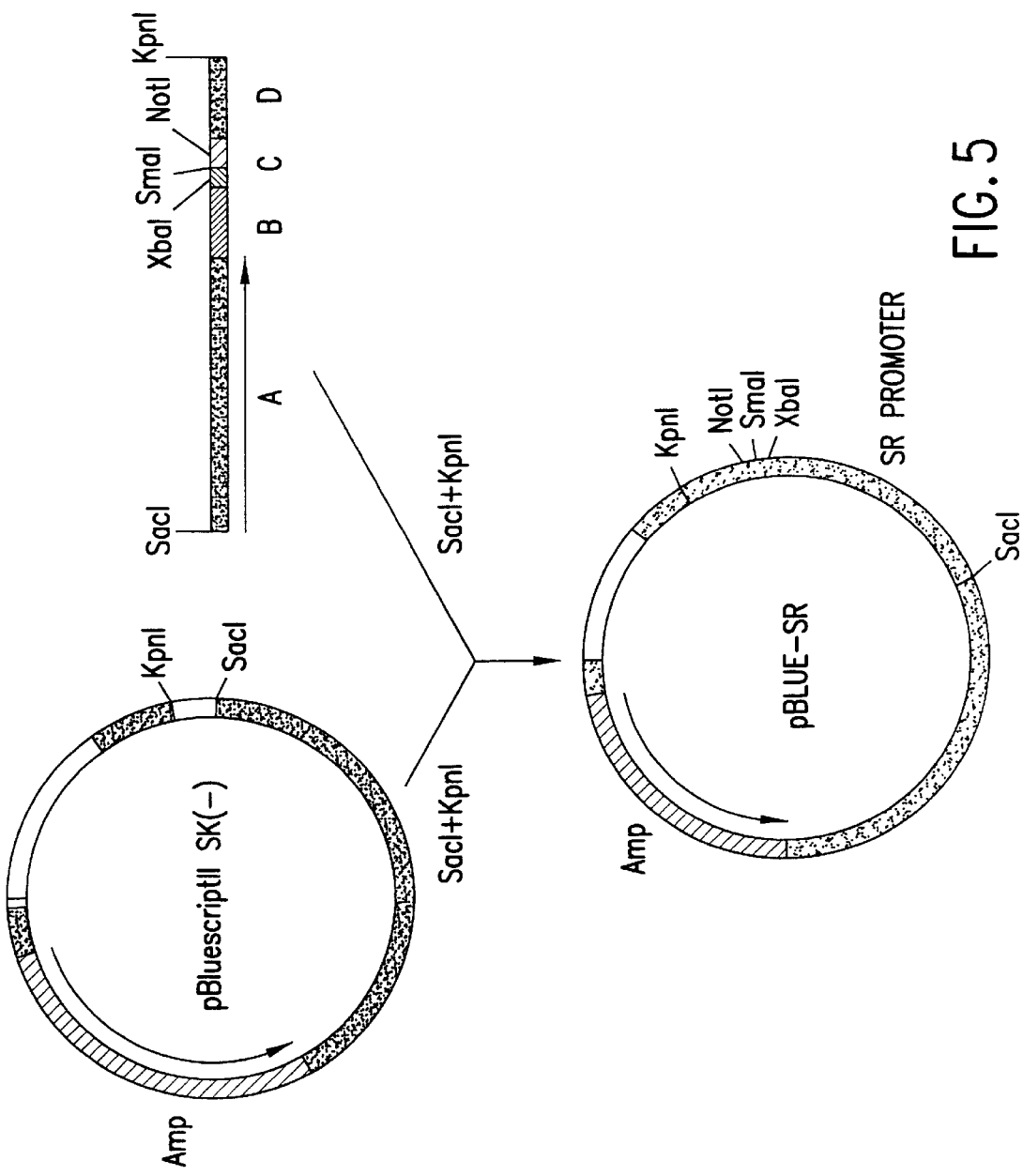
FIG. 5 shows the process of introducing the DNA fragment comprising four regions to construct vector pBlue-SR.

2. Construction of expression vector for cDNA library construction (1) Construction of pBlue-SR A vector that utilizes pcDL-SRα296 (Takebe Y. Mol. Cell. Biol. 8, 466–472 (1988)) as the DNA region necessary for expression in animal cells was constructed. pcDL-SRα296 is known for highly efficient expression in various kinds of cultured cells. The unit for driving transcription was reconstructed by the gene fusion method using PCR (Vallete, F. et al., Nucleic Acids Res. 17, 723–733 (1989)). After the SRα promoter (Fragment A), splicing site (Fragment B), multiple cloning site (MCS) (Fragment C), and polyadenylation signal (Fragment D) were prepared by PCR, these fragments were fused. More specifically, the first PCR was performed using the synthetic DNAs shown in FIG. 2 as primers, the annealing product of the four synthetic DNAs shown in FIG. 3 as the template for the multiple cloning site (MCS), and pcDL-SRα296 as the template for the other regions. FIG. 4 shows the process of linking DNA fragments containing the four regions by PCR. Since the DNA primers used for linking each DNA fragment were designed to have the sequence of the DNA to be amplified at its 3' end and have the sequence of the adjacent DNA to be connected at its 5' end, four amplified DNA fragments (A, B, C, and D) have overlapping parts (30 to 40 bp) between two adjacent regions. These DNA fragments were separated by low-melting point agarose gel electrophoresis and purified with a tip for isolating and purifying nucleic acid, QIAGEN-tip 5 (FUNAKOSHI, QIAGEN Inc.). After equal volumes of Fragments A and B were mixed, Fragment AB was prepared by PCR with outside primers (Primers SRI and SR6). Fragment CD was prepared through a similar process with Primers SR3 and SR8. Finally, Fragment ABCD (about 1 kb) was prepared with equal volumes of purified Fragments AB and CD by PCR with outside primers (Primers SR1 and SR8). The resulting Fragment ABCD was digested with SacI and KpnI whose sites were made outermost in said fragments to purify and recover about 1 kb SacI-KpnI Fragment ABCD. The Fragment ABCD was ligated with about 3 kb SacI-KpnI fragment of pBluescript II SK(−) (TOYOBO, STRATAGENE). The ligation product was introduced into E. coli and cloned. FIG. 5 shows the plasmid DNA pBlue-SR thus obtained.

(2) Construction of pSROL

To apply the Lac repressor system that was reported to enable inducible expression in animal cells (Mickey, C.-T. Cell 48, 555–566 (1987)), a vector plasmid, PSROL, was constructed by modifying pBlue-SR.

(2-1) Construction of pBlue-SRα-Hind

Figure 8:
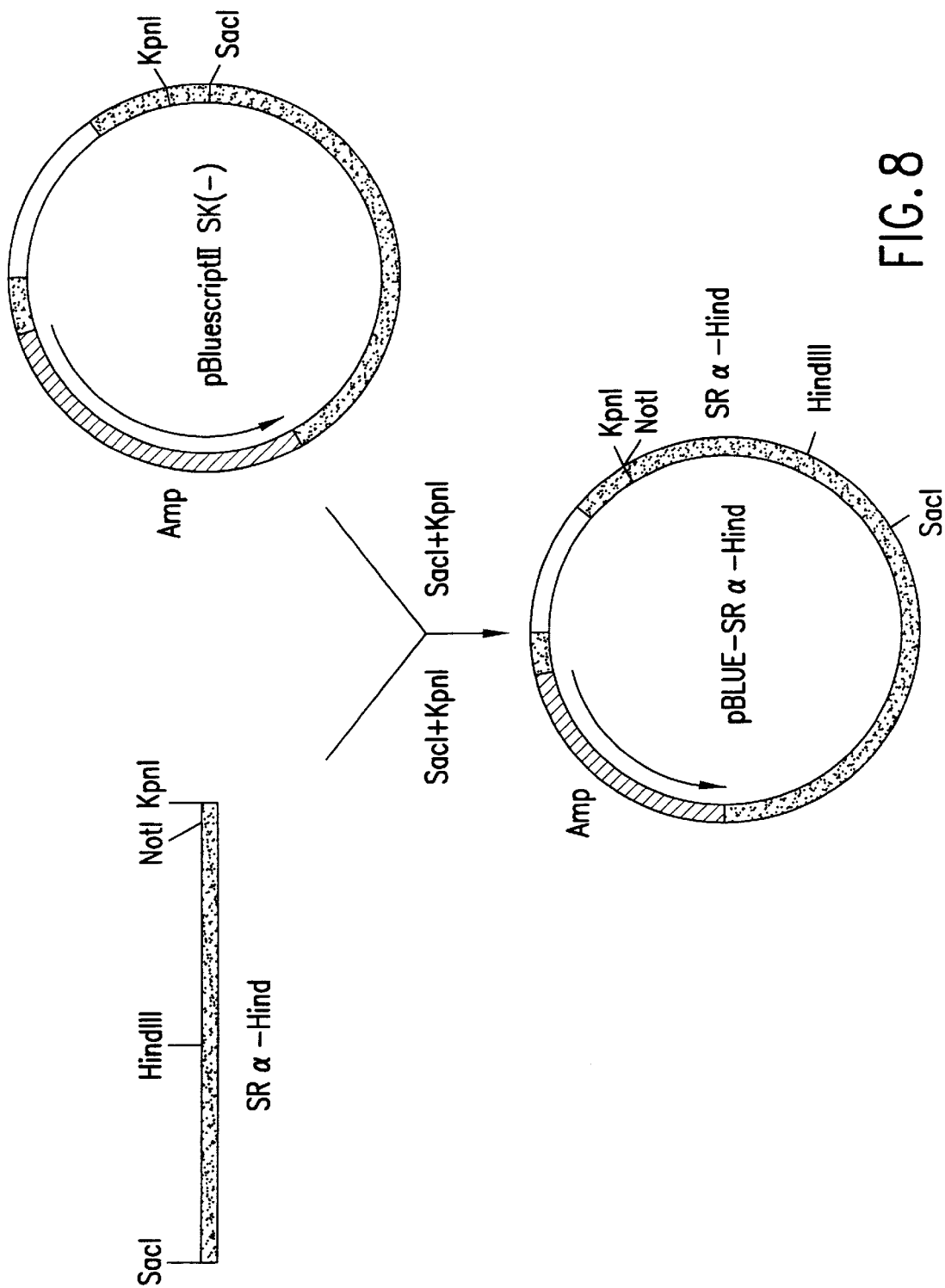
FIG. 8 shows the process of constructing vector pBlue-SRα-Hind.

The position of Lac operator sequence between a promoter and a gene is thought to be important for regulating expression with Lac repressor (Brown, M. Cell 49, 603–612 (1987)). SRα promoter consists of SV40 early promoter fused with the LTR of HTLV-1 (Mol. Cell. Biol. (1988) 466–472). A HindIII site was introduced immediately before the transcription initiation site within the SV40 early promoter region, which exists upstream to the junction between two units of SR α promoter, by mutagenesis using PCR (Higuchi, R. PCR Protocols, Academic Press, Inc. 177–183 (1990)) in order to insert the Lac operator sequence into this HindIII site. An SRα promoter fragment with a HindIII site was prepared using the synthetic DNAs shown in FIG. 6 as the primers and pBlue-SRα as the template. FIG. 7 shows the sequence of the prepared DNA. The detailed process of the construction is described below. The first PCR was performed with the primer pair, SRO-1 and SRO-2 (or SRO-3 and SRO-4) using the pBlue-SRα plasmid DNA as the template. Each PCR product was recovered by low-melting point agarose gel electrophoresis and purified with a tip for isolating and purifying nucleic acid, QIAGEN-tip 5 (FUNAKOSHI, QIAGEN Inc.). The reaction mixture contained a PCR buffer (10 mM Tris-HCl, pH 8.3, 50 mM KCl, 1.5 mM MgCl$_2$, 0.001% gelatin), and 0.2 mM each (final concentration) of dNTPs (DATP, dCTP, dGTP, and dTTP). Twenty cycles of incubation at 94° C. for 1 minute, 55° C. for 1 minute, and 72° C. for 1 minute were performed. In the second PCR, after two cycles were performed for a mixture with equal amounts of the two DNA fragments amplified in the first PCR, additional 18 cycles were performed with Primers SRO-1 and SRO-4 under the same conditions as described above. The resulting PCR product was digested with restriction enzymes SacI and KpnI, purified, and sub-cloned into pBluescript II SK(−) (FUNAKOSHI) which had been digested with the same restriction enzymes. The thus obtained clone plasmid was named pBlue-SRα-Hind (FIG. 8), and its nucleotide sequence was determined.

(2-2) Construction of pBlue-SRα-lacO

Figure 9:
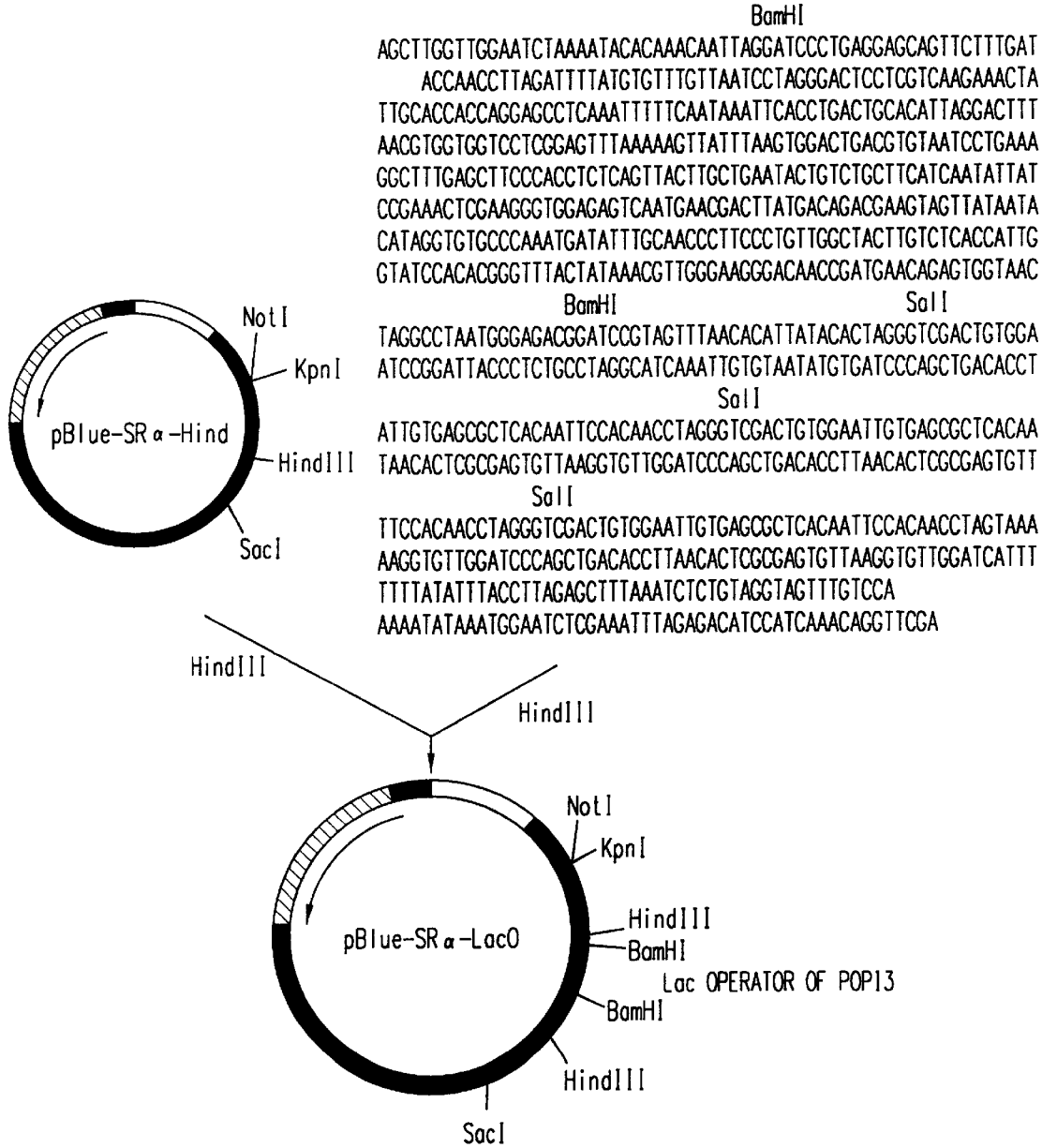
FIG. 9 shows the process of constructing vector pBlue-SRα-lacO.

The plasmid obtained in 1) above was digested with HindIII, and a DNA fragment (about 3.5 kb) was recovered. Separately, pOP13 (TOYOBO, STRATAGENE) was also digested with HindIII to recover a DNA fragment (about 500 bp). This DNA fragment contains three Lac operator sequences. These two fragments were ligated, and the competent cells of E. coli K-12 strain, XL1-Blue, were transformed with the ligation product. The thus-obtained colonies were cultivated, and isolated plasmids were analyzed. Thus, pBlue-SRα-lacO, in which the operator was inserted in the same direction as SRα promoter, has been constructed (FIG. 9).

Figure 10:
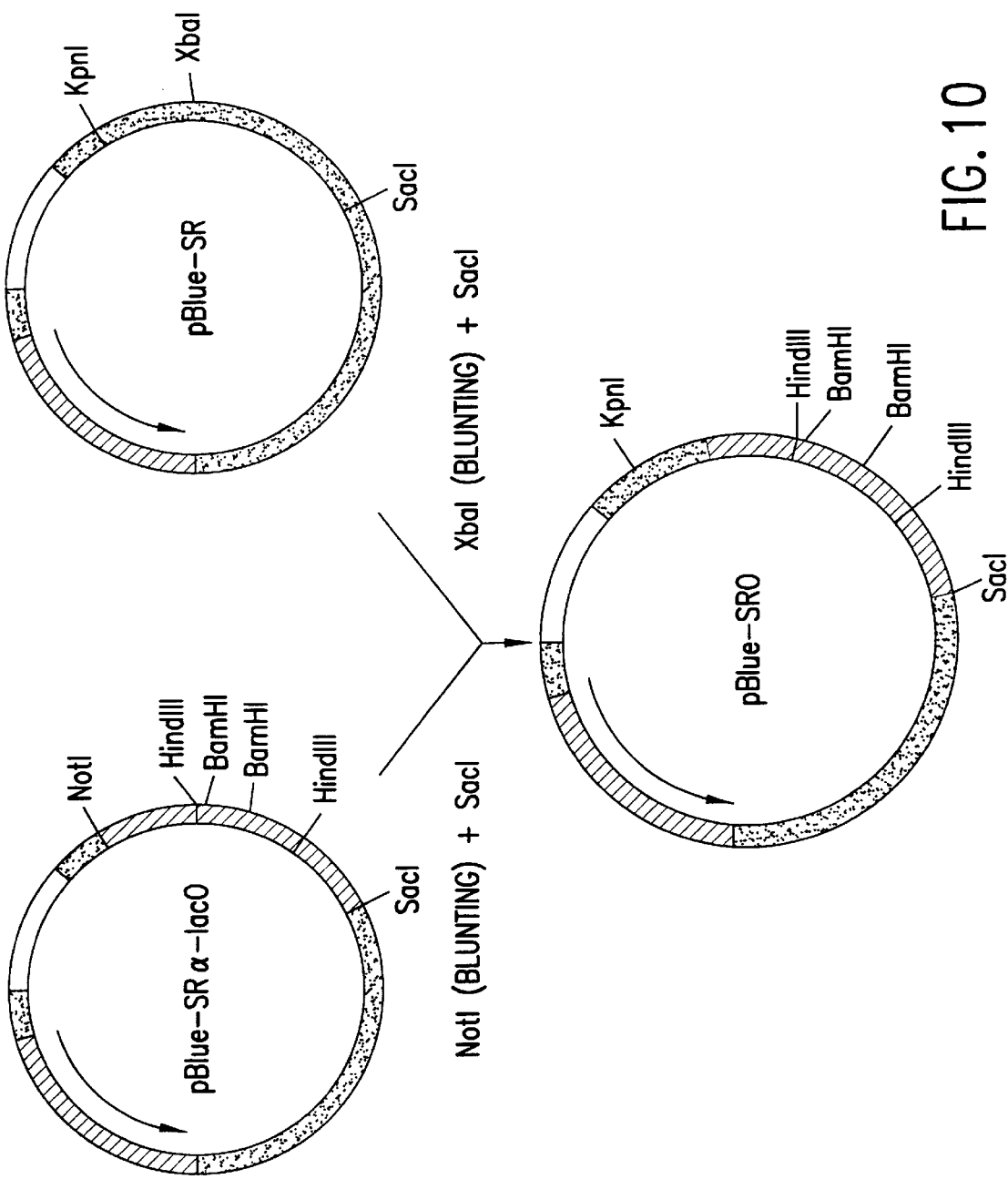
FIG. 10 shows the process of constructing vector pBlue-SRO.

(3) Construction of pBlue-SRO pBlue-SRα-lacO was digested with NotI, blunted, and digested with SacI to obtain a DNA fragment (about 1 kb). Separately, pBlue-SR was digested with SacI and XbaI (for blunting) to obtain a DNA fragment (about 3.2 kb). These two fragments were ligated to each other. By analyzing the clones obtained by transformation with the ligated fragments, pBlue-SRO was constructed (FIG. 10).

(4) Construction of pBlue-SROL
(4-1) Construction of pBlue-Luc pGV-CS (TOYO INK), a cassette vector of the luciferase gene, was digested with Xho I, blunted, and digested with BamHI. Separately, pBluescript II SK(+) (TOYOBO, STRATAGENE) was digested with XbaI (for blunting) and digested with BamHI. By ligating these two DNA fragments, plasmid pBlue-Luc, in which the luciferase gene was subcloned, was constructed.

Figure 11:
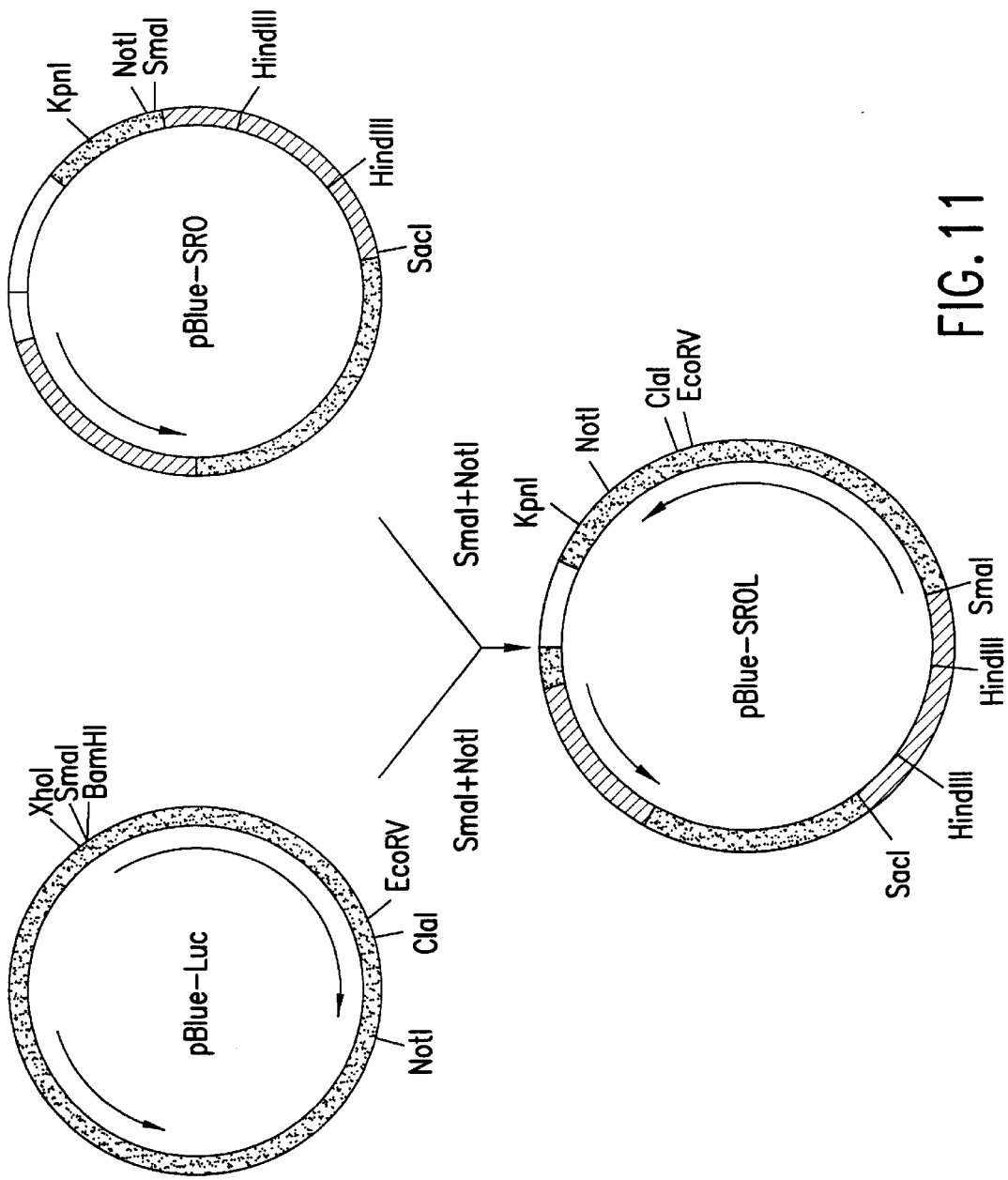
FIG. 11 (SEQ ID NOS 26–27, respectively) shows the process of constructing vector pBlue-SROL.

(4-2) Construction of pBlue-SROL pBlue-SRO was digested with SmaI and NotI to obtain a DNA fragment (about 4.2 kb). Separately, pBlue-Luc was digested with NotI and SmaI, and a DNA fragment (about 1.8 kb) containing the luciferase gene was purified. These two fragments were ligated, and the competent cells of E. coli K-12 strain, XL1-Blue, were transformed with the ligation product. The obtained colonies were cultivated and isolated plasmids were analyzed. Thus, pBlue-SROL, in which the luciferase gene was inserted downstream to the SRα promoter, was constructed (FIG. 11).

(5) Construction of pSROL-3'SS(NB2)
(5-1) Construction of p3'SS(-Xma I)

p3'SS (TOYOBO, STRATAGENE) was linearized by XmaI digestion, blunted with DNA Ligation Kit (TAKARA), and self-ligated. The competent cells of E. coli K-12 strain, XL1-Blue, were transformed with the resulting plasmid. The obtained colonies were cultivated, and isolated plasmids were analyzed to obtain p3'SS(-Xma I) with no XmaI site. The purpose of this treatment is to disrupt the Xma I site within the DNA derived from p3 ' SS for constructing the cDNA library later.

(5-2) Construction of pSROL-3'SS(NB2)

Figure 12:
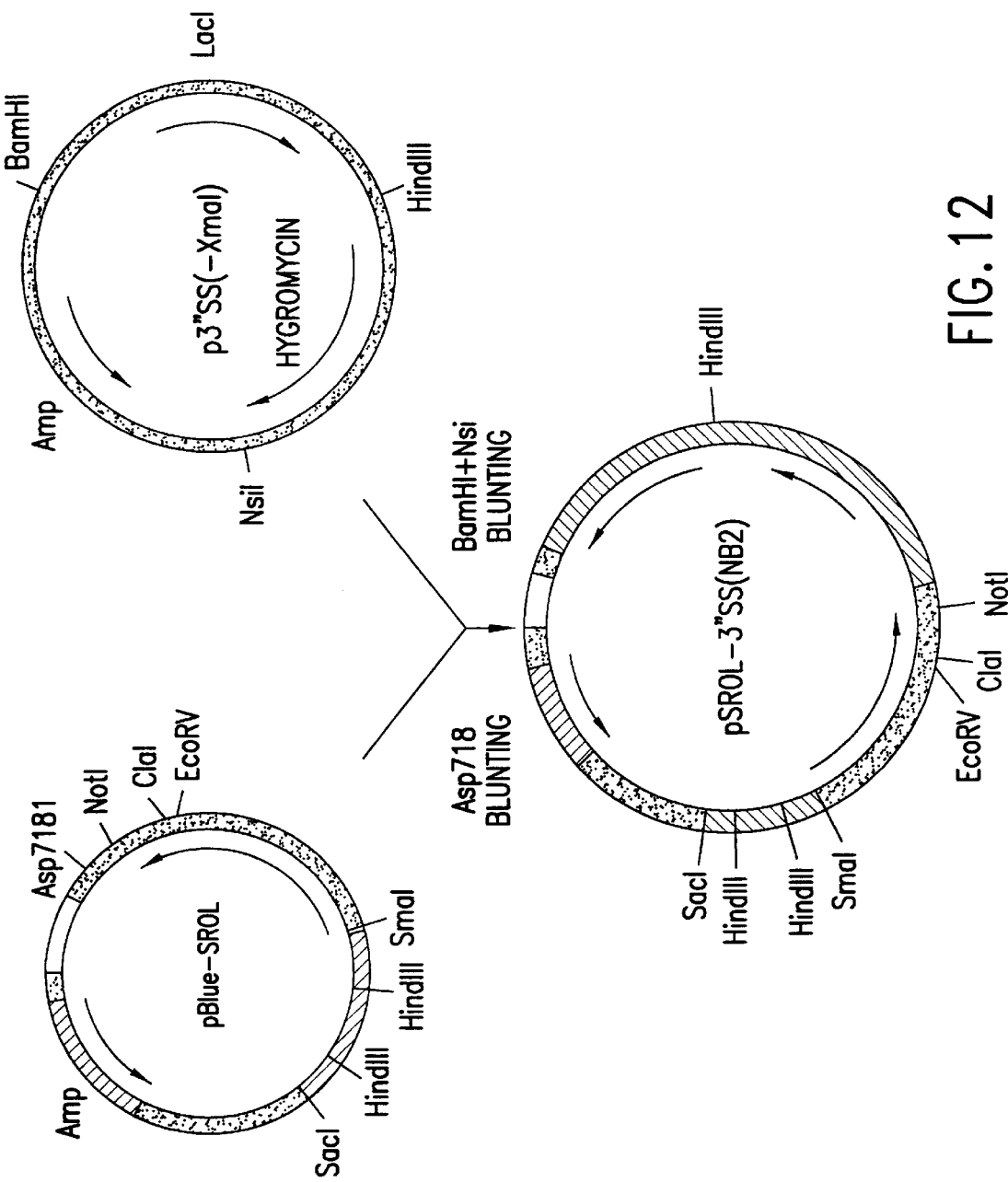
FIG. 12 shows the process of constructing vector pSROL-3'SS (NB2).

A DNA fragment (about 4.3 kb) generated by digesting p3 'SS(-Xma I) with BamHI and NsiI was recovered by low-melting point agarose gel electrophoresis and purified with a tip for isolating and purifying nucleic acid, QIAGEN-tip 5 (FUNAKOSHI, QIAGEN Inc.). This fragment comprises units for expressing the hygromycin resistance gene and the Lac repressor. The hygromycin resistance gene is a selective marker used in gene transfer to animal cells, and the Lac repressor acts on Lac operator sequence. Separately, pBlue-SROL was digested with Asp718 and purified in the same manner as described above. These two fragments were blunted with a DNA Blunting Kit (TAKARA) then ligated with a DNA Ligation Kit (TAKARA). The ligation product was introduced into the competent cells of E. coli K-12 strain, XL1-Blue, to thereby obtain colonies resistant to ampicillin. The plasmids from the thus-obtained clones were analyzed, and pSROL-3'SS(NB1) and pSROL-3'SS(NB2) were obtained. In these two plasmids, the BamHI-NsiI fragment derived from p3'SS(-Xma I) was inserted in different directions. pSROL-3'SS (NB2) (FIG. 12), in which the direction of transcription from the three genes (the luciferase gene, the hygromycin gene, and the Lac repressor gene) is the same, was used in the experiments below.

3. Construction of cDNA Library for Cloning
(1) Preparation of Poly(A)$^+$ RNA

About $2 \times 10^8$ MRC-5 SV1 TG1 cells (Riken Cell Bank) were cultivated for 5 hours after addition of $1 \times 10^{-6}$ M dexamethasone (DEX). About 5 mg of RNA was extracted from the cells by the Acid Guanidium Thiocyanate Phenol Chloroform (AGPC) method (Chomczynski, P. and Sacchi, N. Anal. Biochem. 162, 156–159 (1987)). About 15 μg of poly(A)$^+$ RNA was purified from 500 μg of the RNA using Oligotex-dT30 (TAKARA). This purification procedure was repeated twice.

(2) Preparation of Vector DNA

After being digested with NotI, pSROL-3'SS(NB2) was dephosphorylated at its ends by Bacterial Alkaline Phosphatase (BAP) (TAKARA) treatment then digested with SmaI. A 8.5 kb desired DNA fragment was recovered by low-melting point agarose gel electrophoresis.

(3) Synthesis of cDNA and Construction of Library

The process from the first-strand cDNA synthesis to ligation with a vector was performed in accordance with the "Method for Gene Library Construction" (Experimental Medicine: SUPPLEMENT, BIOMANUAL SERIES 2, YODOSHA, 79–94) using a ZAP-cDNA SYNTHESIS KIT (TOYOBO, STRATAGENE) as reagents as follows. M-MuLV Reverse Transcriptase synthesized 2.6 μg of first-strand cDNA using 10 μg of the poly(A)$^+$ RNA described above as the template. The second-strand cDNA was then synthesized using E. coli RNase H and E. coli DNA polymerase. The resulting DNA was blunted with T4 DNA polymerase and digested with NotI. Low molecular weight DNAs were purified on a CHROMASPIN-400 column (TOYOBO, Clontech). Finally, 0.6 μg of double-stranded DNA was obtained. The thus-obtained cDNA was ligated using T4 DNA ligase into pSROL-3'SS (NB2) digested with SmaI and Not I ((2) described above). The reaction mixture was mixed with E. coli DH10B strain (ELECTRO MAX DH10B cell, GIBCO BRL) to introduce the cDNA into the cells using the CELL-PORATOR system (GIBCO BRL). It has been revealed that the library comprises 1.6×10⁶ colonies as a whole. Moreover, 90% of the clones contained the cDNA insert.

Figure 13:
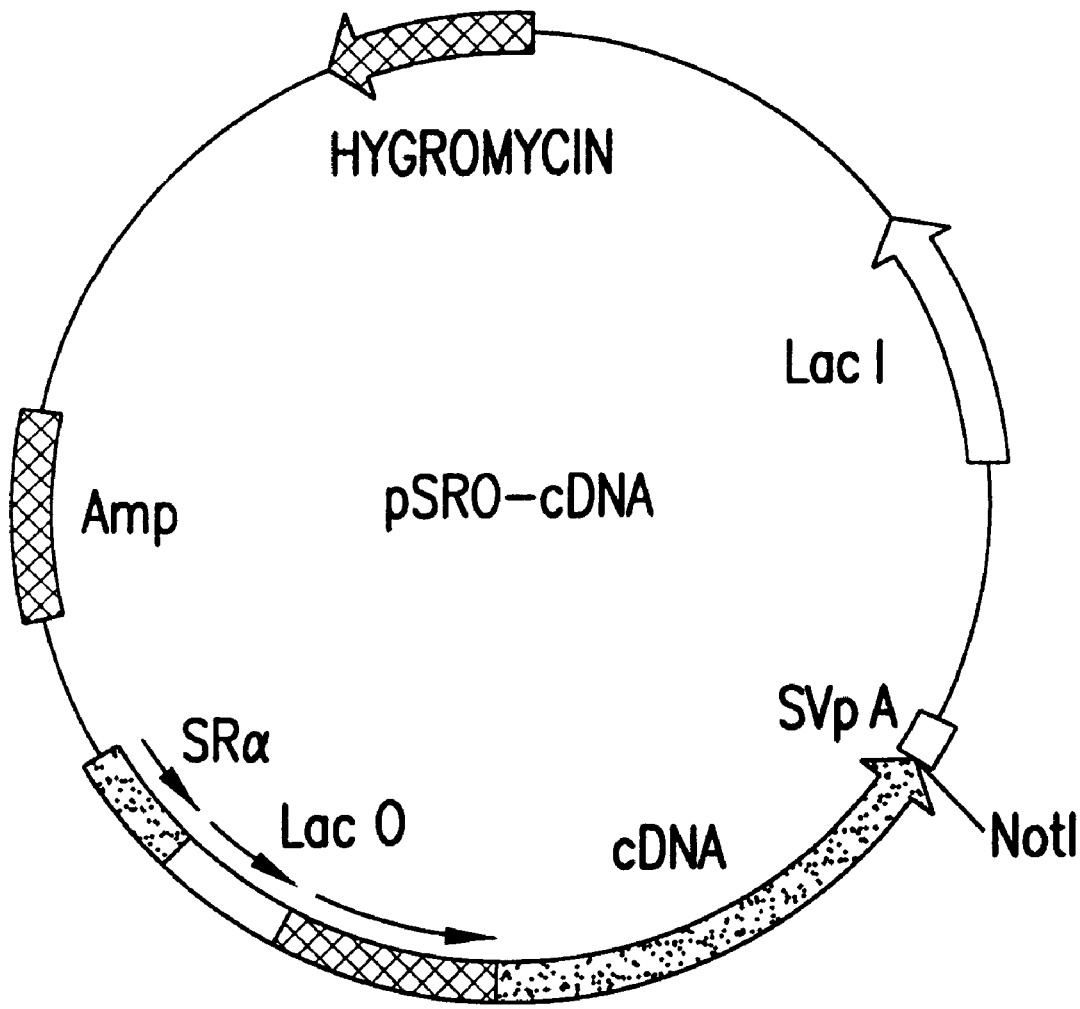
FIG. 13 shows the structure of vector pSRO-cDNA.

FIG. 13 shows the structure of the plasmid with cDNA constructed as described above. The plasmid can be used to incorporate cDNA of an antiinflammatory protein and transfected into animal cells to express the protein in the cells.

This vector can be used not only for transient expression of proteins coded by the cDNAs but also for obtaining stable (permanent) transfectants because it has the hygromycin resistance gene as. a selective marker. When luciferase cDNA was used as an example of cDNA, a sufficient amount of protein (luciferase) was produced (expressed).

4. Construction of the Luciferase Expression Vector, pIL8p-Luc

Figure 14:
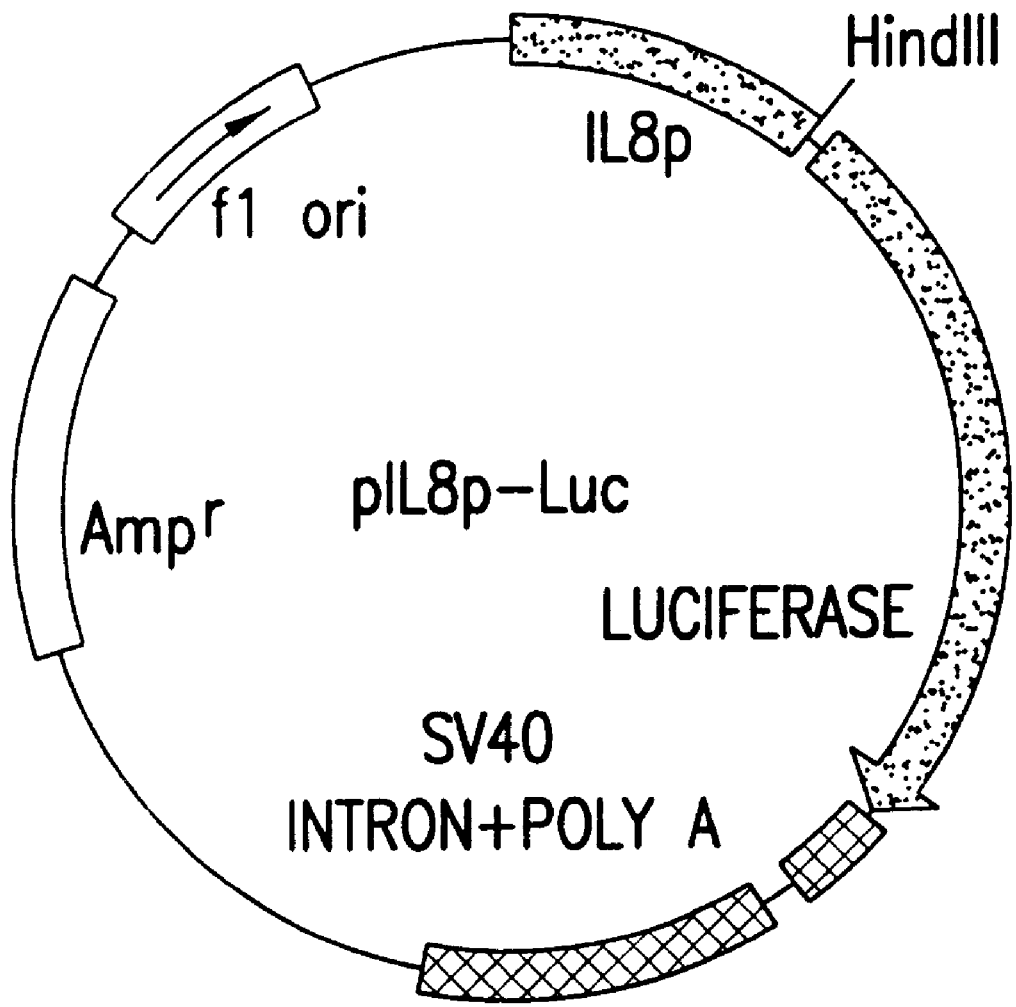
FIG. 14 shows the structure of reporter plasmid vector pIL8p-Luc.

DNA comprising the human IL-8 (neutrophil chemotactic cytokine) promoter region (Matsushima, K. et al., J. Imm. 143, 1366–1371 (1989)) prepared by PCR using a genomic DNA of human VA-13 cells (Riken Cell Bank) was digested with HincII and HindIII to obtain a DNA fragment of −546 to +44 (IL8p). This fragment (IL8p) was inserted into pGL2-Promoter Vector (Promega) whose SV40 early promoter was removed with SmaI and HindIII, producing pIL8p-Luc. FIG. 14 shows the structure of this plasmid.

5. Cell Cultivation

MRC-5 SV1 TG1 cells (Riken Cell Bank), known as HGPRT-deficient cells, were cultivated in RITC 80-7 medium supplemented with 10% FCS. Dexamethasone dissolved in 100% ethanol was diluted with the same medium and added to the culture. Ethanol alone was added to the control group in the same concentration as ethanol added to the dexamethasone-treated group.

6. Quantitative Measurement of the Survival Rate of Cells

Cell survival was judged by quantitatively measuring the amount of the reduced product of Alamar Blue (KANTO KAGAKU), which was taken into cultured cells, in terms of fluorescence intensity or absorbance. This compound is reduced in theliving cells and linked with the NADPH production system. The reduction product emits a characteristic color or fluorescence to be measured. After cells were cultivated in a 96-well plate, the medium was renewed, Alamar Blue was added, and the cells were incubated for 3 hours. The luminescence (fluorescence) at 590 nm was then measured by exciting the culture supernatants at 530 nm with a CytoFluor 2350 (MILLIPORE).

7. Establishment of HGPRT-deficient Cell Clone that Stably Maintains the gpt Gene with the IL-8 Promoter pREP9-IL8p-gpt-neo (FIG. 1), which had the gpt gene fused with the human IL-8 promoter and the neomycin resistance gene neo, was digested with ClaI and SphI to remove ori and EBNA-1 regions derived from the EB virus vector (pREP9) and to open the circular structure. MRC-5 SV1 TG1 cells deficient in HGPRT were transfected with the thus-obtained linearized DNA (IL8p-gpt-neo), which was made easy to integrate into the chromosome, and screened with 400 μg/ml G418. Twenty-one clones were isolated using cloning syringes. These clones were cultivated on a 12-well plate at a concentration of about 5×10⁴ cells/ml, treated with 1 μM dexamethasone for 3 hours, then cultivated with 1000 ng/ml 6-TG under stimulation by 20 to 100 U/ml (1 to 5 ng/ml) TNF-α.

In two of these clones (#17 and #21), cell death was induced by TNF-α stimulation in the presence of 6-TG and inhibited by treatment with dexamethasone.

Based upon the results above, a method quantitatively superior to the method for judging the effect of dexamethasone by observing cell survival under a microscope (e.g., a method for judging survival of cells by quantitatively measuring the amount of the reduction product of Alamar Blue (KANTO KAGAKU) which has been taken into cultured cells in terms of fluorescence intensity or absorbance) was tested. This compound is reduced in cells, linked with the NADPH production system, and emits characteristic color or fluorescence. The test was performed as follows.

Figure 15:
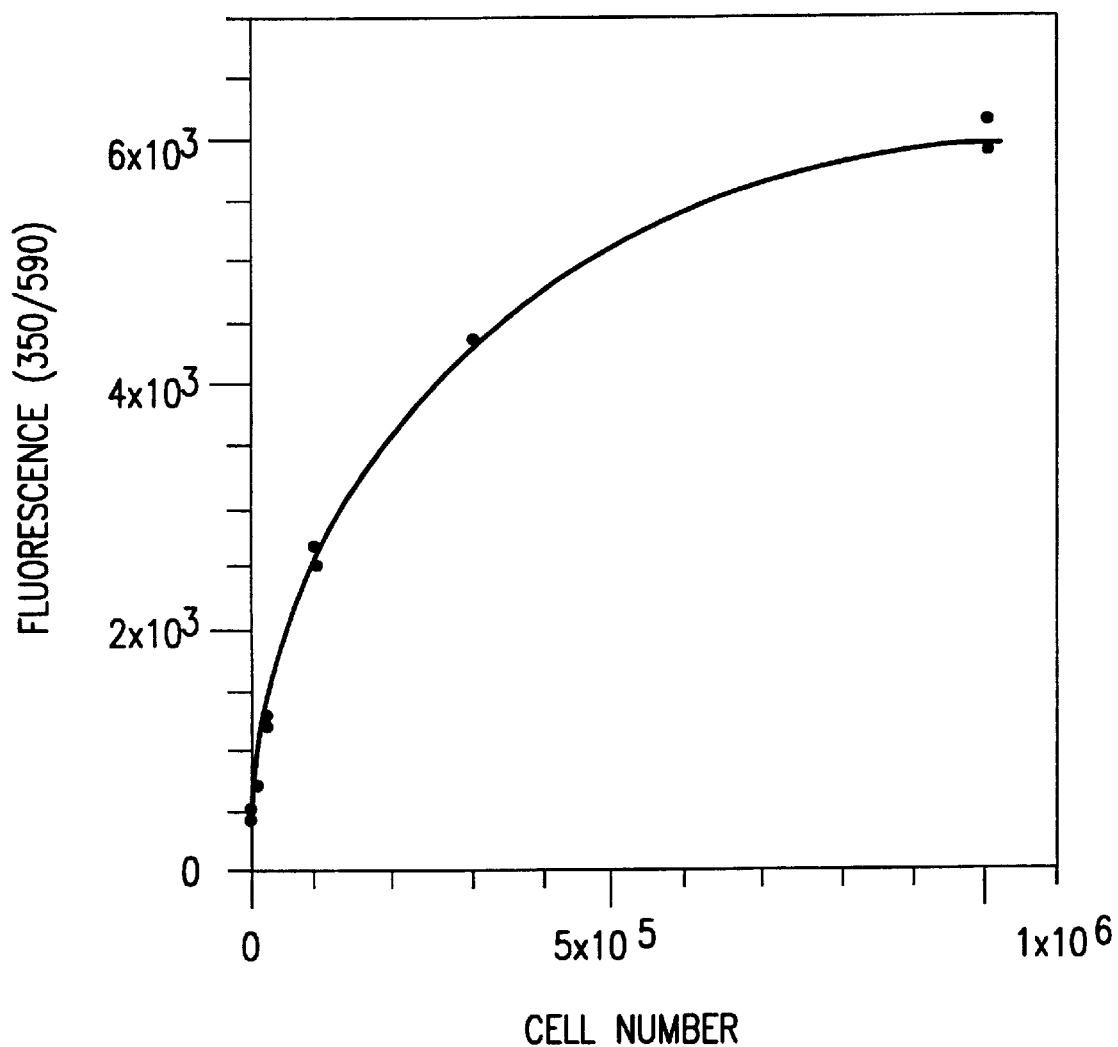
FIG. 15 shows the result of measuring living cells using Alamar Blue.

After 10⁶ MRC-5 SV1 TG1 cells, deficient in HGPRT, were cultivated in a 96-well plate, the medium was exchanged, Alamar Blue was added, and the cells were incubated for 3 hours. The luminescence (fluorescence) at 590 nm was then measured by exciting the culture supernatants at 530 nm with a CytoFluor 2350 (MILLIPORE) (FIG. 15).

Figure 16:
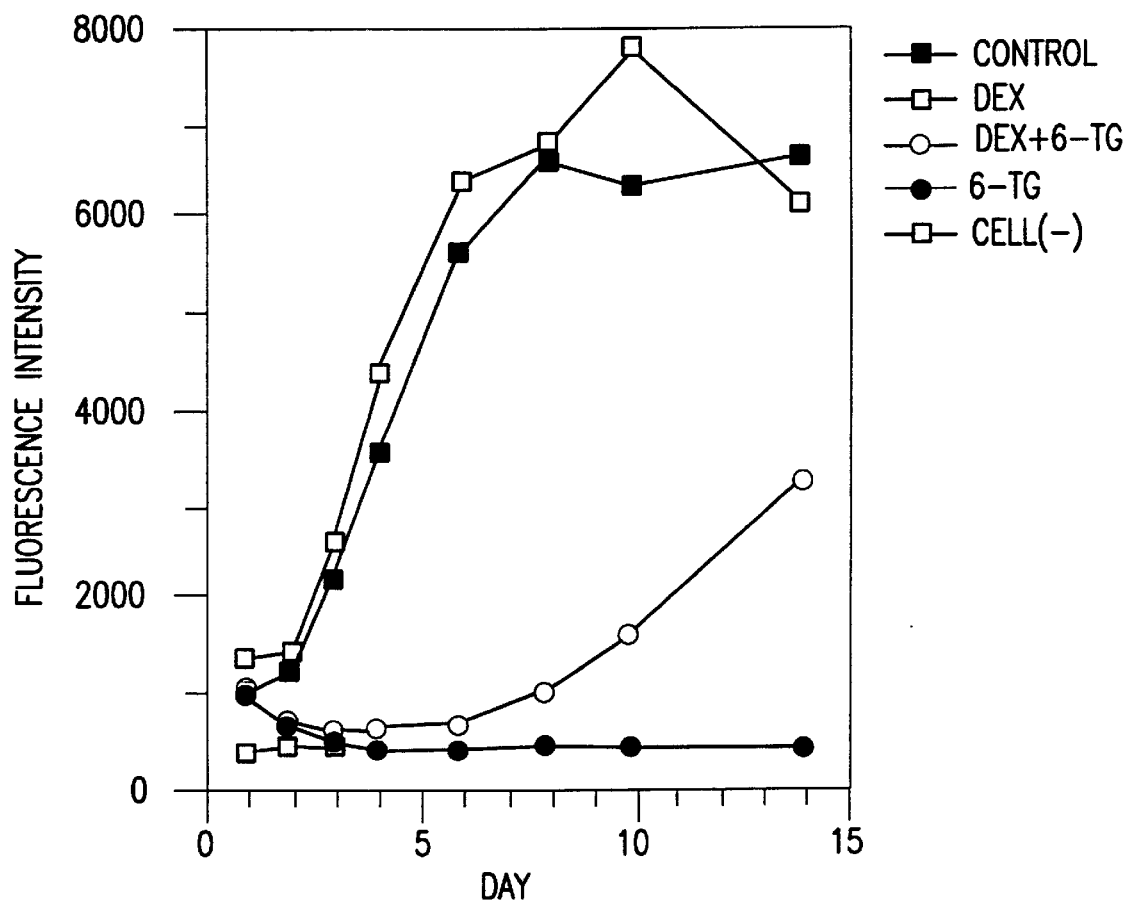
FIG. 16 shows the effect of extracellular stimulation factor (TNF-α) and dexamethasone treatment on proliferation of cell clone IL8p-gpt-neo#17.

Based upon the results, 5×10³ cells of Clone #17 (IL8p-gpt-neo #17), which stably maintained IL8p-gpt-neo, were cultivated in a 96-well plate, and living cells were quantitatively measured using Alamar Blue by adding 1000 U/ml TNF-a in the presence of 1 μM dexamethasone and 1 μg/ml 6-TG. The results are shown in FIG. 16 and reveal that the cells of Clone #17 (IL8p-gpt-neo #17), which stably maintains IL8p-gpt-neo, all died when 6-TG was added and TNF-α stimulation applied, and that dexamethasone inhibited cell death and kept cells growing. Thus, the cell clone IL8p-gpt-neo #17, which dies if IL-8 promoter is activated by TNF stimulation but which is rescued from the cell death by treatment with antiinflammatory steroid, has been developed by stably introducing the gpt gene with the IL-8 promoter into HGPRT-deficient cells. This cell clone can be used as a system for assessing cDNA encoding an antiinflammatory protein that inhibits the activation of the IL-8 promoter. Clone #17 (IL8p-gpt-neo #17), which stably maintains IL8p-gpt-neo, was deposited with the National Institute of Bioscience and Human-Technology, Agency of Industrial Science and Technology, Ministry of International Trade and Industry (accession number FERM BP-5706).

8. First Screening of cDNA Library (pSRO-cDNA Library) Using HGPRT-deficient Cell Clone IP8p-gpt-neo #17 which Stably Maintains IL8p-gpt-neo The first screening was performed by introducing the pSRO-cDNA library into IL8p-gpt-neo #17 cells (FIG. 16). Since the plasmids have the hygromycin resistance gene as the marker, only cells into which the plasmids are introduced survive by hygromycin selection. In contrast, the cells die if TNF-α and 6-TG are added to the culture medium. However, if the pSRO-cDNA library has a cDNA encoding protein that inhibits the activation of the IL-8 promoter (antiinflammatory protein), cells in which the cDNA is expressed must survive. The experiment was performed as follows.

250 μg of pSRO-cDNA library (size 1.6×10⁶) was introduced into IL8p-gpt-neo #17 cells (2.5×10⁷ cells; five 500 cm² trays) using Transfectam. Twodayslater,100 μg/ml hygromycin was added. Five days thereafter, 20 mM IPTG was added, and the next day, 200 U/ml TNF and 1 μg/ml 6-TG were added to conduct screening. Consequently, several colonies per tray survived. Twenty-two clones were isolated on the twelfth day after addition of TNF and 6-TG and cultivated in the presence of hygromycin. Finally, cells of 16 strains were obtained.

9. Isolation of cDNAs Obtained in the First Screening

Genomic DNA was isolated from the 16 strains obtained in the first screening, and the pSRO-cDNA-library-derived cDNA insert introduced into the genomic DNA was extracted by PCR as described below.

1) Genomic DNA was prepared with a QIAamp Blood kit (QIAGEN).

Figure 17:
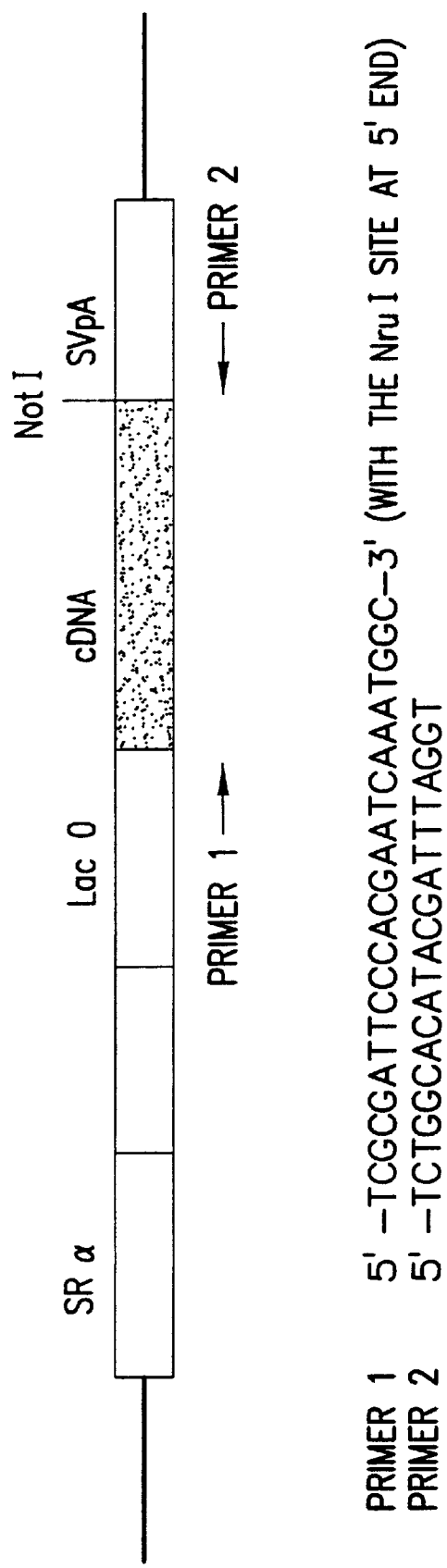
FIG. 17 shows the PCR primers (SEQ ID NOS 30–31, respectively) for isolating cDNA derived from the pSRO-cDNA library introduced into the genomic DNA of the cells.

2) PCR was performed using the Ex Taq (TaKaRa) and Gene Amp PCR system 9600 (Perkin Elmer) for 30 cycles of incubation at 96° C. for 60 seconds, at 60° C. for 30 seconds, and at 72° C. for 30 seconds, followed by incubation at 72° C. for 6 minutes. Sequences immediately before the cDNA (a part of LacO sequence) and immediately after the NotI site (a part of SVpA sequence) in pSRO-cDNA (FIG. 13) were used as PCR primers (FIG. 17).

Agarose gel electrophoresis revealed that nine kinds of PCR products were obtained from genomic DNAs isolated from 5 out of the 16 strains described above.

Next, these PCR products were digested with Nru I and Not I, and ligated with the purified fragments generated by digesting pSROL-3'SS(NB2) with SmaI and NotI. The ligation product was introduced into competent cells of E. coli JM109 to obtain colonies resistant to ampicillin. The plasmids from the colonies were analyzed. Expression vector pSRO-cDNA (FIG. 13), which corresponds to nine kinds of cDNAs collected by PCR, was thus selected.

The nucleotide sequences of the nine kinds of pSRO-cDNA were analyzed. The second screening was performed as shown below. 10. Second screening by reporter gene method The second screening was performed for cDNAs obtained in the first screening to confirm the inhibitory effect on the IL-8 promoter. The second screening was performed by the reporter gene method in which pIL8p-Luc (FIG. 14) was used as a luciferase expression vector having the IL-8 promoter.

If pSRO-cDNA, the expression vector of the cDNA obtained in the first screening (FIG. 13), and pIL8p-Luc are co-transfected at a ratio of 10:1, cells taking pIL8p-Luc also take the target cDNA expression vector into themselves (Analytical Biochemistry 188, 245–254 (1990)). Therefore, in this system, whether or not introducing the expression vector of the cDNA to be tested can inhibit the activation of the IL-8 promoter by TNF-α stimulation was examined. Furthermore, pSV β (CLONTECH, 6178-1), the expression vector of β-galactosidase, was used as the internal reference for compensating the transfection efficiency of the expression vectors.

On the first day, 2×10$^5$ cells of IL8p-gpt-neo #17 were cultivated on a six-well plate. On the second day, transfection was performed using Transfectam by adding 1 μg of cDNA to be tested (pSRO-cDNA, FIG. 13), 0.1 μg of IL8p-Luc (FIG. 14), and 0.2 μg of psvβ (internal reference) per well. Three to four wells were used for every cDNA. On the third day, IPTG was added to 20 mM (final concentration). On the fourth day, 1 μM dexamethasone (final concentration) was added. After three hours, TNF was added to 100 U/ml (final concentration). After five hours, cells were collected with a cell lysis agent LCβ (TOYO INK), and cell lysate was prepared. The luciferase activity in the lysate was then measured with PicaGene (TOYO INK). β-galactocidase activity was also measured with Galacto-Ligt (TROPIX) after endogenous galactocidase activity was eliminated by heating the cell lysate at 48° C. for 50 minutes. pSRO without cDNA was used as the control of pSRO-cDNA. The data were shown in terms of luciferase activity compensated by β-galactocidase activity (internal reference).

Figure 18:
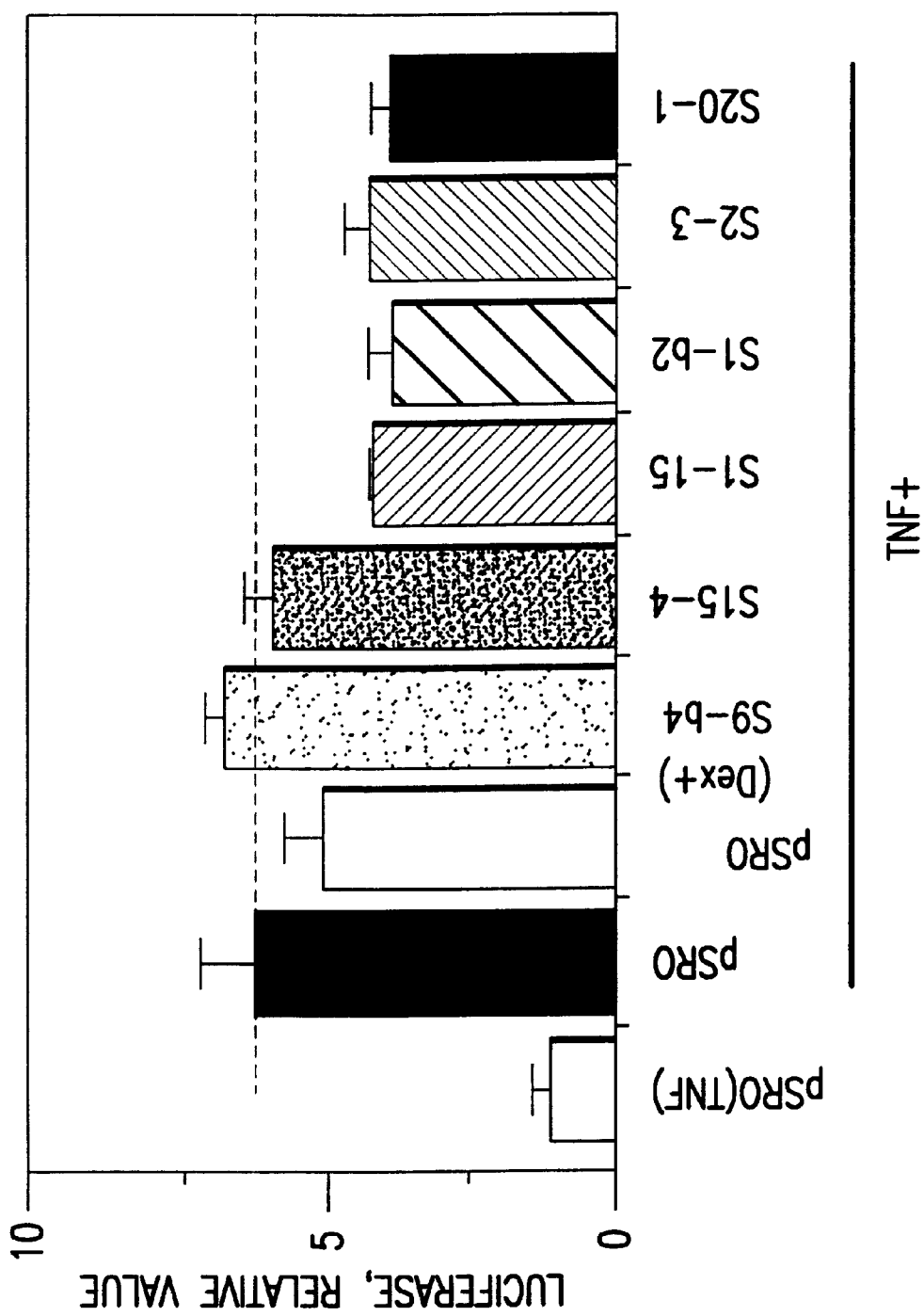
FIG. 18 shows the result of using the reporter gene to detect the inhibitory activity on the IL-8 promoter of cDNA isolated by the method of the present invention.

Consequently, TNF induced strong luciferase activity in the cells into which pSRO without cDNA was introduced, whereas treatment with dexamethasone inhibited the activity (FIG. 18). In the test cDNAs, S1-15, S1-b2, S2-3, and S20-1 showed inhibitory activity on the IL8 promoter, but S9-b4 and S15-4 showed no inhibitory activity (FIG. 18). Example 2 Analysis of "S1-15" clone S1-15 was selected by the second screening using the reporter gene and found to show inhibitory activity on the IL-8 promoter reproducibly. S1-15 was analyzed as follows. 1. Analysis of the Structure of S1-15

Sequencing of S1-15 revealed that it was a 637 bp DNA fragment. The sequence is described in SEQ ID NO: 2, and the amino acid sequence deduced therefrom is described in SEQ ID NO: 1. A homology search by algorithms of "Smith-Waterman" ((GENE BRIGHT), Hitachi Soft-Engineering) in the database of GenBank, based on the sequence of the DNA fragment, detected two genes (HIP116 and 6D3). HIP116 encodes the transcriptional regulatory factor that binds to the transcription initiation site of human immunodeficiency virus (HIV)-1 and the SPH motif of the SV40 enhancer. This transcriptional regulatory factor was found to consist of 1009 amino acid residues and to have an estimated molecular weight of 114 kDa (Philip L. et al., The Journal of Biological Chemistry, Vol. 270, 4575–4587 (1995)). 6D3 encodes the transcriptional regulatory factor isolated as the factor binding to the 5' upstream site of the plasminogen activator inhibitor-1 (PAI-1) gene.

Figure 19:
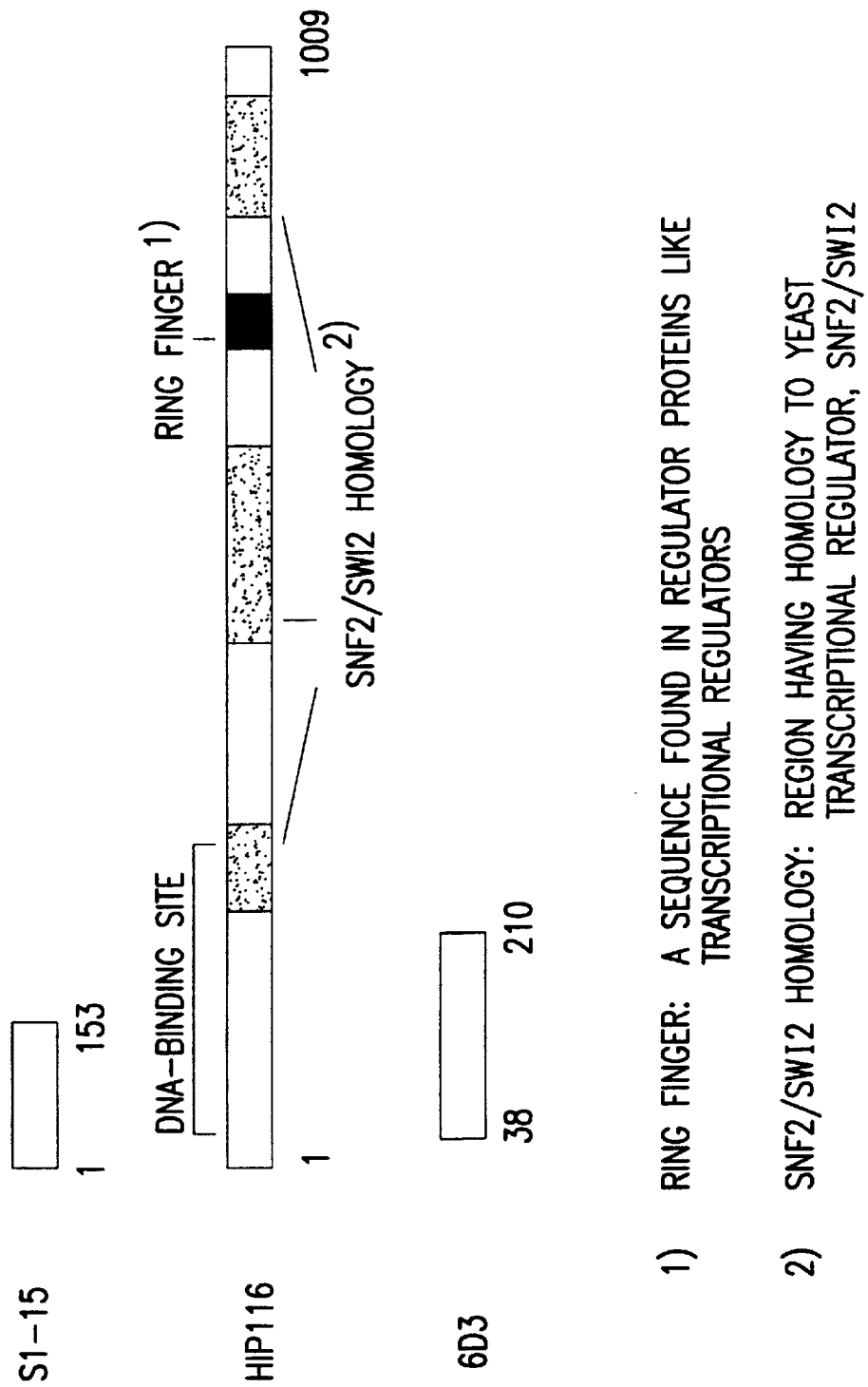
FIG. 19 compares the amino acid sequence of the transcriptional inhibitory factor S1-15 of the present invention and two transcriptional inhibitory factors (HIP116, 6D3) detected by homology search.

Comparing the deduced amino acid sequence of S1-15 and the amino acid sequence of HIP116 revealed that S1-15 has the same sequence as the 1st to 152nd amino acids of 1009 amino acid residues of HIP116 except that the 102nd amino acid, asparagine, was replaced by serine (FIG. 19). Therefore, S1-15 encodes the transcriptional regulatory factor lacking most of the C-terminus. The 38th to 152nd amino acid residues of HIP116 were considered to be the region binding to DNA upon transcription (Philip L. et al., The Journal of Biological Chemistry Vol. 270, 4575–4587 (1995)) (FIG. 19). S1-15 encodes the region corresponding to the DNA binding region of HIP116 except for the 37 amino acid residues at the N-terminus. Though 6D3 does not comprise the whole DNA binding region (the 38th to 152nd amino acid residues) described in the above reference, it reportedly binds to the 5' upstream site of the PAI-1 gene (Verhandlingen-Koninklijke, Academie Voor Genees Kunde Van Belgie, 55, 225–264 (1993)). Therefore, the DNA binding region of these transcriptional regulatory factors presumably varies depending on the DNA sequence to which the transcriptional regulatory factors are bound. S1-15, which also does not comprise the whole DNA binding region of HIP116, is thought to possess activity binding to the upstream site of the IL-8 gene.

The regions homologous to SNF2/SWI2 in HIP116 and Ring Finger are thought to interact with other transcriptional factors. "S1-15" completely lacks this region (FIG. 19).

Figure 20:
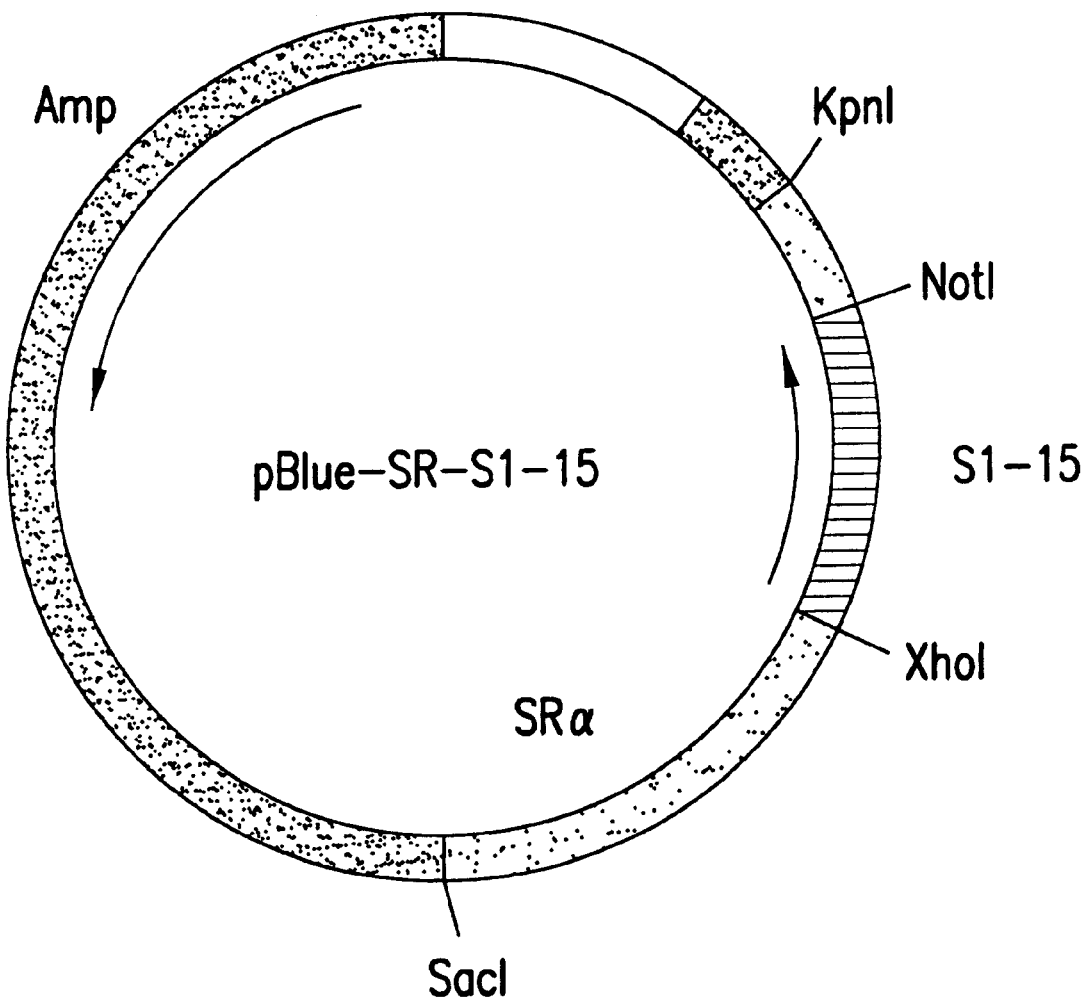
FIG. 20 shows the structure of vector pBlue-SR-S1-15.
Figure 21:
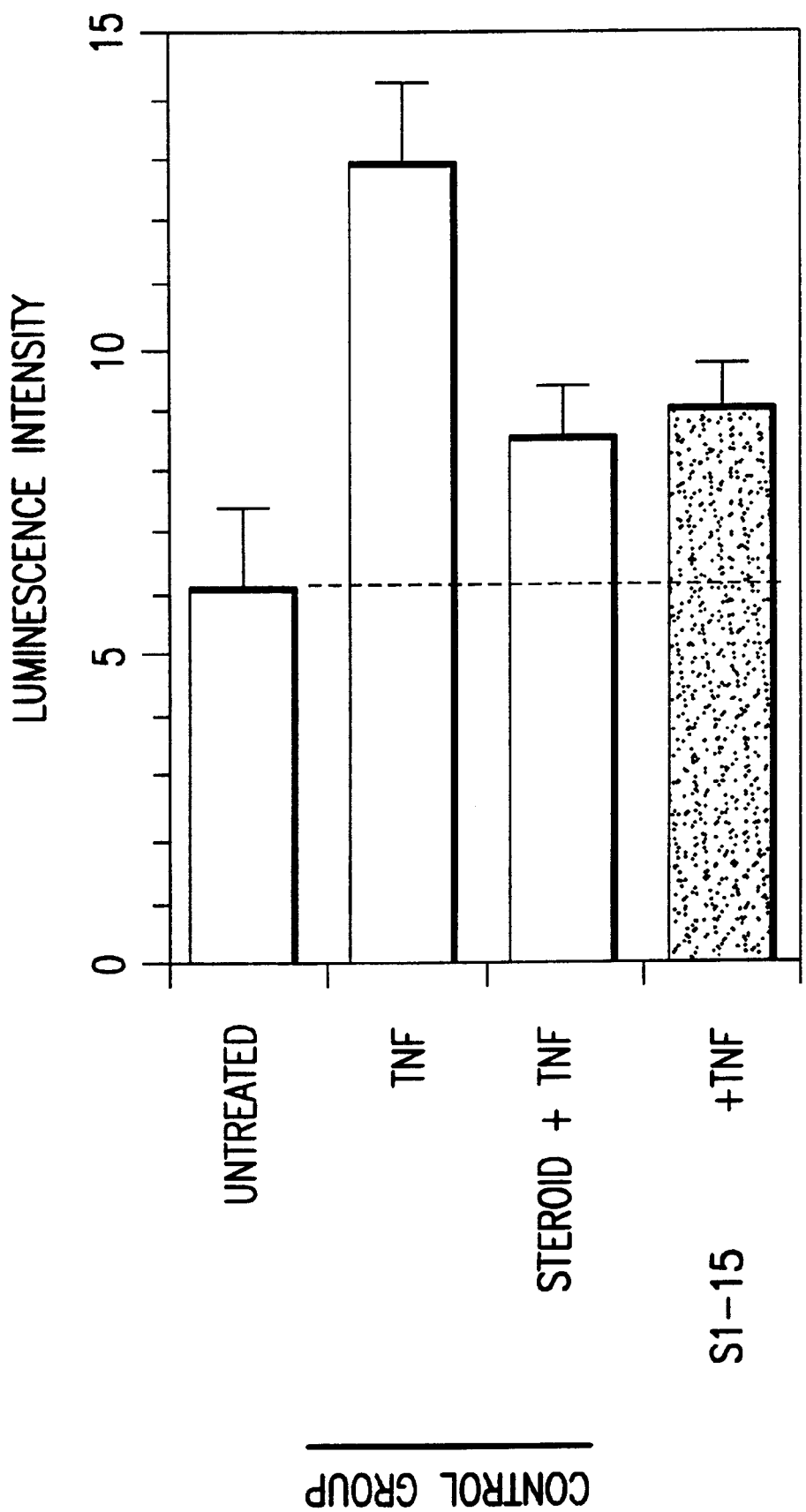
FIG. 21 shows the inhibitory activity of S1-15 for the IL-8 promoter detected using the reporter gene.

Analysis of the S1-15 sequence revealed that the sequence derived from the vector was added to the 3' end of S1-15. The expression vector without the vector-derived sequence, pBlue-SR-S1-15 (FIG. 20), was constructed and analyzed by the reporter gene method described above. The IL-8 promoter-inhibitory activity was also detected in pSRα/S1-15, which lacked the vector-derived amino acid sequence (FIG. 21).

Figure 22:
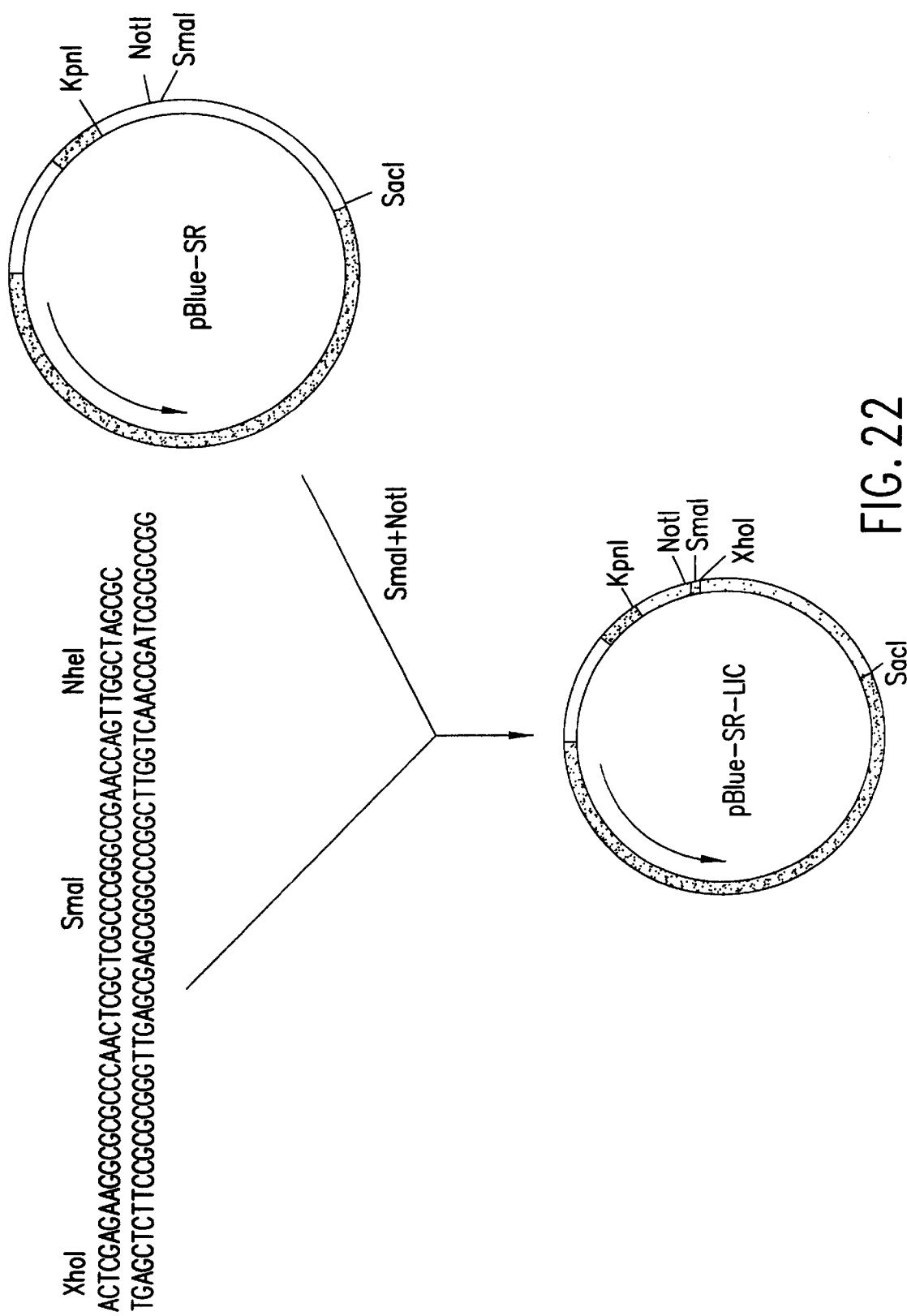
FIG. 22 (SEQ ID NOS 30–31, respectively) shows the process of constructing pBlue-SR-Lic used to construct vector pBlue-SR-S1-15.
Figure 23:
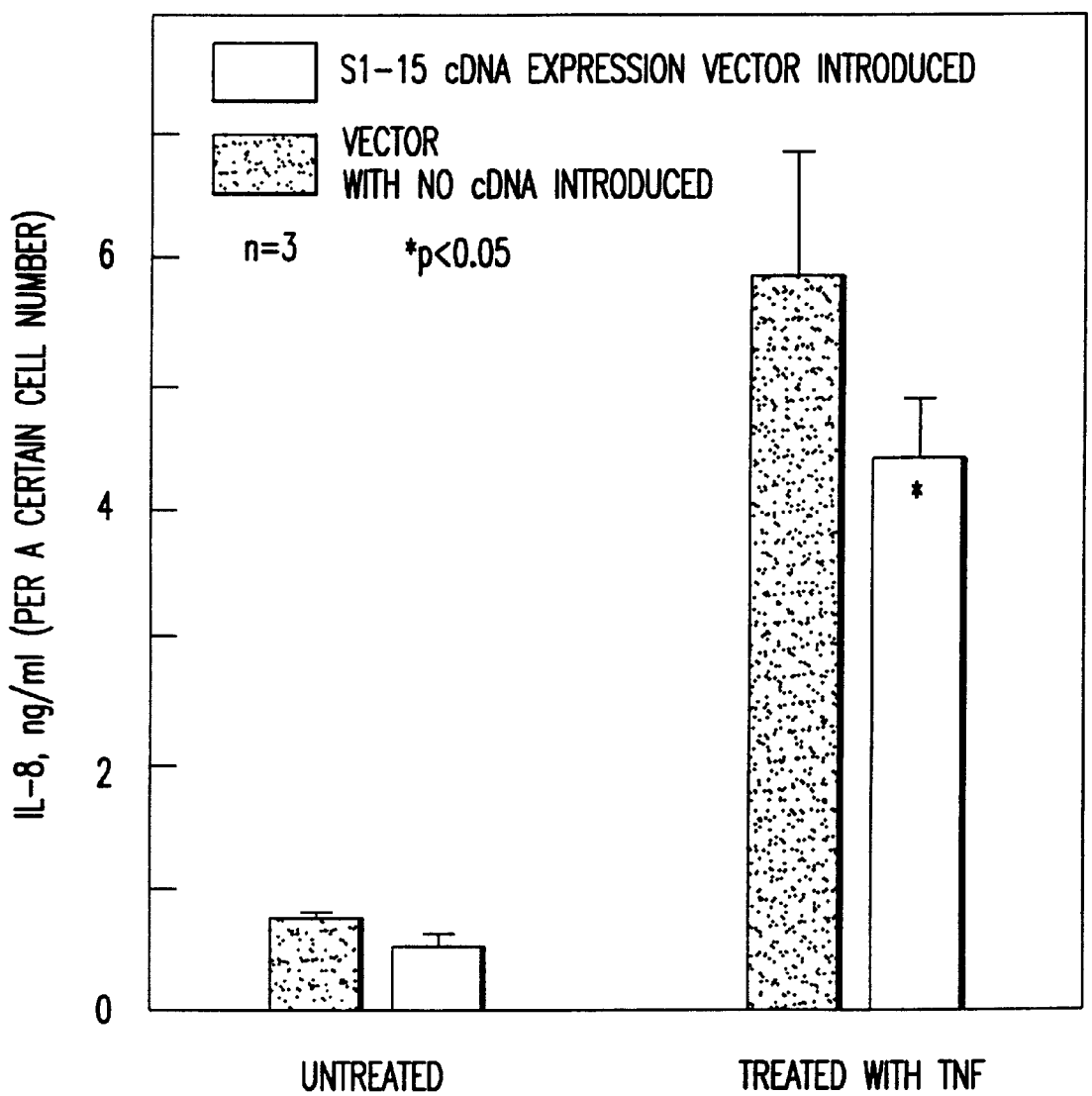
FIG. 23 shows the inhibitory activity of S1-15 on the IL-8 promoter detected by expressing the IL-8 gene.

FIG. 22 shows the method of constructing pBlue-SR-S1-15. pBlue SR plasmid digested with SmaI and NotI was ligated with a synthetic DNA (LIC linker) depicted in FIG. 22 to construct plasmid pBlue-SR-LIC. S1-15 was inserted into the vector by the ligation independent cloning (LIC) method (Aslanidis, C. Nucleic Acids Res. 18: 6069–6074 (1990)). Specifically, pBlue-SR-LIC was digested with SmaI; recovered by low melting point agarose gel electrophoresis; purified by a nucleic acid separation/purification tip, "QIAGEN-tip 5" (Funakoshi, QIAGEN Inc.); and treated with T4 DNA polymerase in the presence of dATP. Separately, PCR was performed using the S1-15 gene-containing plasmid as the template, the primer (SEQ ID NO: 7) (5'-CTCGCTCGCCCACGCTCCTCTTGTCATCCCAC-3'), and the primer (SEQ ID NO: 8) (5'-CTGGTTCGGCCCATTATCCCCAAAAAGTCATCTG-CAGA-3'). The PCR product was recovered by low melting point agarose gel electrophoresis, purified by nucleic acid separation/purification tip "QIAGEN-tip 5" (Funakoshi, QIAGEN Inc.), and treated with T4DNA polymerase in the presence of dTTP. Two DNA fragments treated with T4 DNA polymerase were annealed, and the annealing product was introduced into competent cells of E. coli strain K-12 XL1-Blue to obtain ampicillin resistant colonies. The desired sequence was confirmed to be inserted into the clones, thereby obtaining vector pBlue-SR-S1-15 capable of expressing S1-15 (FIG. 20). 2. Confirmation of IL-8 production inhibitory activity of "S1-15" obtained by the second screening The inventors examined whether or not introducing the S1-15 expression vector inhibited IL-8 production of MRC-5 SV1 TG1 cells when stimulated by TNF-α.

pBLUE-SR-S1-15 and pHook-1 (Invitrogen) were cotransfected to MRC-5 SV1 TG1 cells, and the transfectants were collected by a magnet with Capture-Tec Kit (Invitrogen). pBlue-SR-LIC, which is the control, was cotransfected with pHook-1 (Invitrogen). After 24 hours, IL-8 produced in the culture supernatants was measured by ELISA. The S1-15 transfectants produced less IL-8 than the control (FIG. 23).

3. Purification of S1-15 Protein
(1) Preparation of Expression Vector pGEX/S1-15

PCR was performed using "pSRO/S1-15" as the template, the primer (5'-ATGTCGACTCAGCGCCATGTCCTGGA-TGTTC-3') (SEQ ID NO: 9), and the primer (5'-GTCACGATGCGGCCGCCCAAAAAGTCATATG-CAGAGGCATG-3') (SEQ ID NO: 10). The PCR product was digested with SalI and NotI and inserted into vector pGEX-5X-1 (Pharmacia), which was digested with SalI and NotI, to obtain expression vector pGEX/S1-15. E. coli JM109 was transformed with pGEX/S1-15.

(2) Purification of S1-15 Protein

E. coli carrying pGEX/S1-15 was cultured at 28° C. for one day. After 0.1 mM IPTG was added to the medium, culturing was performed for an additional 4 hours. The cells were collected and lysed in 6M urea. The supernatant obtained by centrifugation was diluted to a urea concentration of 2M, and the dilution was allowed to be absorbed by glutathione sepharose 4B. After the absorbent was washed, GST/S1-15 was eluted with glutathione. The eluate was dialyzed against 200 mM urea/100 mM NaCl/20 mM Tris pH 8.0 then against 100 mM NaCl/20 mM Tris pH8.0/2 mM $CaCl_2$.

(3) Peptide Mapping by LC-MS

GST/S1-15 was digested with trypsin and analyzed by LC-MS to confirm that GST/S1-15 protein was constructed as designed.

Industrial Applicability

The present invention provides a protein having the transcriptional inhibitory activity and lacking at least a part of regions other than those having DNA binding activity of transcriptional regulatory factors.

If expression of a specific gene correlates with a disease, the protein of the present invention can be used to treat the disease. In particular, the protein of the present invention is expected to be applied to gene therapy considering its high gene specificity.

What is claimed is:

1. An isolated polypeptide comprising the amino acid sequence of SEQ ID NO:1, wherein said polypeptide directly binds to DNA and inhibits transcription of interleukin 8 gene.

2. The isolated polypeptide of claim 1, wherein said polypeptide lacks at least a part of a transcriptional activation region which interacts with a transcription initiation complex involved in transcription.

3. An isolated polypeptide consisting of the amino acid sequence of SEQ ID NO: 1.

4. A method of inhibiting transcription of the interleukin 8 gene comprising:
 (i) introducing, into cells, the polypeptide of claim 1 in an amount effective enough to inhibit transcription of the interleukin 8 gene, and
 (ii) binding said polypeptide to a promoter or enhancer of the interleukin 8 gene in cells.

5. A method of inhibiting transcription of the interleukin 8 gene comprising:
 (i) introducing into cells, the polypeptide of claim 2 in an amount effective enough to inhibit transcription of the interleukin 8 gene, and
 (ii) binding said polypeptide to a promoter or enhancer of the interleukin 8 gene in cells.

6. A method of inhibiting transcription of the interleukin 8 gene comprising:
 (ii) introducing into cells, the polypeptide of claim 3 in an amount effective enough to inhibit transcription of the interleukin 8 gene, and
 (ii) binding said polypeptide to a promoter or enhancer of the interleukin 8 gene in cells.

* * * * *

UNITED STATES PATENT AND TRADEMARK OFFICE
CERTIFICATE OF CORRECTION

PATENT NO. : 6,355,775 B1
DATED : March 12, 2002
INVENTOR(S) : Nagasawa et al.

It is certified that error appears in the above-identified patent and that said Letters Patent is hereby corrected as shown below:

<u>Drawings,</u>
Fig. 15, please correct the title "FLUORESCENCE (<u>350</u>/590)," to read
-- FLUORESCENCE (530/590) --
Fig. 22, please add -- LIC Linker -- in the upper left corner Signed and Sealed this Second Day of July, 2002

Attest:

JAMES E. ROGAN
Attesting Officer    Director of the United States Patent and Trademark Office

SEQUENCE LISTING

<160> NUMBER OF SEQ ID NOS: 31

<210> SEQ ID NO 1
<211> LENGTH: 153
<212> TYPE: PRT
<213> ORGANISM: Homo sapiens

<400> SEQUENCE: 1

Met Ser Trp Met Phe Lys Arg Asp Pro Val Trp Lys Tyr Leu Gln Thr
 1               5                  10                  15

Val Gln Tyr Gly Val His Gly Asn Phe Pro Arg Leu Ser Tyr Pro Thr
            20                  25                  30

Phe Phe Pro Arg Phe Glu Phe Gln Asp Val Ile Pro Pro Asp Asp Phe
        35                  40                  45

Leu Thr Ser Asp Glu Glu Val Asp Ser Val Leu Phe Gly Ser Leu Arg
    50                  55                  60

Gly His Val Val Gly Leu Arg Tyr Tyr Thr Gly Val Val Asn Asn Asn
65                  70                  75                  80

Glu Met Val Ala Leu Gln Arg Asp Pro Asn Asn Pro Tyr Asp Lys Asn
                85                  90                  95

Ala Ile Lys Val Asn Ser Val Asn Gly Asn Gln Val Gly His Leu Lys
            100                 105                 110

```
Lys Glu Leu Ala Gly Ala Leu Ala Tyr Ile Met Asp Asn Lys Leu Ala
        115                 120                 125

Gln Ile Glu Gly Val Val Pro Phe Gly Ala Asn Asn Ala Phe Thr Met
    130                 135                 140

Pro Leu His Met Thr Phe Trp Gly Lys
145                 150

<210> SEQ ID NO 2
<211> LENGTH: 637
<212> TYPE: DNA
<213> ORGANISM: Homo sapiens
<220> FEATURE:
<221> NAME/KEY: CDS
<222> LOCATION: (179)..(637)

<400> SEQUENCE: 2
cggcgtcgac gtctgactgg actcgcggcg acttaccttt cagtcgtgcg ctcctgatcc      60
ggcgctcgga atttgtcccc ggcttcaggg ctgcggggcc tggaaggagg cgtatcgagg     120
cggctcgaaa acgatccagg ggagccgagg cgctcctctt gtcatcccac tcagcgcc      178 atg tcc tgg atg ttc aag agg gat cca gtt tgg aag tac ttg cag act      226
Met Ser Trp Met Phe Lys Arg Asp Pro Val Trp Lys Tyr Leu Gln Thr
  1               5                  10                  15 gtc cag tat gga gtt cat gga aat ttt cca cgc ctc tca tat cca act      274
Val Gln Tyr Gly Val His Gly Asn Phe Pro Arg Leu Ser Tyr Pro Thr
             20                  25                  30 ttc ttt cca cgt ttt gaa ttc caa gat gtt atc cct cca gat gac ttt      322
Phe Phe Pro Arg Phe Glu Phe Gln Asp Val Ile Pro Pro Asp Asp Phe
         35                  40                  45 cta act agt gat gaa gaa gta gat tcc gtt tta ttt gga agt ttg aga      370
Leu Thr Ser Asp Glu Glu Val Asp Ser Val Leu Phe Gly Ser Leu Arg
     50                  55                  60 ggt cat gtg gtt gga cta cgc tat tac acg gga gta gtt aat aat aat      418
Gly His Val Val Gly Leu Arg Tyr Tyr Thr Gly Val Val Asn Asn Asn
 65                  70                  75                  80 gaa atg gtt gca tta caa cga gat cct aat aac cct tat gat aag aat      466
Glu Met Val Ala Leu Gln Arg Asp Pro Asn Asn Pro Tyr Asp Lys Asn
                 85                  90                  95 gca att aaa gta aac agt gtg aat gga aat caa gtt ggc cat tta aag      514
Ala Ile Lys Val Asn Ser Val Asn Gly Asn Gln Val Gly His Leu Lys
            100                 105                 110 aaa gag ctt gca ggt gct ttg gcc tat atc atg gac aac aaa ttg gca      562
Lys Glu Leu Ala Gly Ala Leu Ala Tyr Ile Met Asp Asn Lys Leu Ala
        115                 120                 125 caa att gaa ggg gta gtt cct ttt ggt gca aac aat gct ttt acc atg      610
Gln Ile Glu Gly Val Val Pro Phe Gly Ala Asn Asn Ala Phe Thr Met
    130                 135                 140 cct ctg cat atg act ttt tgg gga aaa                                   637
Pro Leu His Met Thr Phe Trp Gly Lys
145                 150

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
ataagctttt cacatgagcg aaaaataca                                        29
```

```
<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 4
atggatccct attgtaaccc gcctgaagt                              29

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 5
atgtctcgag aattcagtaa cccaggcatt attttatc                    38

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
ttgtcctaga agcttgtgtg ctctgctgtc                             30

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
ctcgctcgcc cacgctcctc ttgtcatccc ac                          32

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 8
ctggttcggc ccattatccc caaaaagtca tctgcaga                    38

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 9
atgtcgactc agcgccatgt cctggatgtt c                           31

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Primer
```

```
<400> SEQUENCE: 10
gtcacgatgc ggccgcccaa aaagtcatat gcagaggcat g                    41

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
atgagctcag aaccagctgt ggaatg                                     26

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 12
ctgttctgcg ccgttacaaa accagaaagt taactg                          36

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 13
ttacttctgc tctaaaagct ggcgcgccct gcagt                           35

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 14
tcacctaaat cgtatgtgcc agacatgata agatacat                        38

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 15
cagttaactt tctggttttg taacggcgca gaacag                          36

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 16
actgcagggc gcgccagctt ttagagcaga agtaa                           35

<210> SEQ ID NO 17
<211> LENGTH: 38
```

```
<212> TYPE: DNA
<213> ORGANISM: Artificial Sequence
<220> FEATURE:
<223> OTHER INFORMATION: Description of Artificial Sequence: Primer

<400> SEQUENCE: 17
atgtatctta tcatgtctgg cacatacgat ttaggtga                      38

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 18
taggtaccgt cgacccctga acctgaaaca taaaa                         35

<210> SEQ ID NO 19
<211> LENGTH: 88
<212> TYPE: DNA
<213> ORGANISM: Artificial Sequence
<220> FEATURE:
<223> OTHER INFORMATION: Description of Artificial Sequence: DNA
        template

<400> SEQUENCE: 19
ggcgcgccct gcagtctaga gaattcccac gaatcaaatg gcccgggcca gaagatgcat    60
ggctcgaggc ggccgcaagc ttctatag                                       88

<210> SEQ ID NO 20
<211> LENGTH: 78
<212> TYPE: DNA
<213> ORGANISM: Artificial Sequence
<220> FEATURE:
<223> OTHER INFORMATION: Description of Artificial Sequence: DNA
        template

<400> SEQUENCE: 20
cacatacgat ttaggtgaca ctatagaagc ttgcggccgc ctcgagccat gcatcttctg    60
gcccgggcca tttgattc                                                  78

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 21
atgagctcag aaccagctgt ggaatg                                   26

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 22
ccgaggcaag cttggcctcg gcctctgcat aaa                           33

<210> SEQ ID NO 23
<211> LENGTH: 33
<212> TYPE: DNA
```

<213> ORGANISM: Artificial Sequence
<220> FEATURE:
<223> OTHER INFORMATION: Description of Artificial Sequence: Primer

<400> SEQUENCE: 23
cgaggccaag cttgcctcgg cctctgagct att                            33

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 24
atggtaccgc ggccgcgtaa cggcgcagaa cagaaaa                        37

<210> SEQ ID NO 25
<211> LENGTH: 634
<212> TYPE: DNA
<213> ORGANISM: Artificial Sequence
<220> FEATURE:
<223> OTHER INFORMATION: Description of Artificial Sequence: DNA insert

<400> SEQUENCE: 25
atgagctcag aaccagctgt ggaatgtgtg tcagttaggg tgtggaaagt ccccaggctc      60
cccagcaggc agaagtatgc aaagcatgca tctcaattag tcagcaacca ggtgtggaaa    120
gtccccaggc tccccagcag gcagaagtat gcaaagcatg catctcaatt agtcagcaac    180
catagtcccg cccctaactc cgcccatccc gcccctaact ccgcccagtt ccgcccattc    240
tccgccccat ggctgactaa ttttttttat ttatgcagag gccgaggcca agcttgcctc    300
ggcctctgag ctattccaga agtagtgagg aggcttttttt ggaggcctag gctttgggct    360
cgcatctctc cttcacgcgc ccgccgccct acctgaggcc gccatccacg ccggttgagt    420
cgcgttctgc cgcctcccgc ctgtggtgcc tcctgaactg cgtccgccgt ctaggtaagt    480
ttaaagctca ggtcgagacc gggcctttgt ccggcgctcc cttggagcct acctagactc    540
agccggctct ccacgctttg cctgaccctg cttgctcaac tctacgtctt tgtttcgttt    600
tctgttctgc gccgttacgc ggccgcggta ccat                               634

<210> SEQ ID NO 26
<211> LENGTH: 467
<212> TYPE: DNA
<213> ORGANISM: Artificial Sequence
<220> FEATURE:
<223> OTHER INFORMATION: Description of Artificial Sequence: DNA
      construct

<400> SEQUENCE: 26
agcttggttg gaatctaaaa tacacaaaca attaggatcc ctgaggagca gttctttgat      60
ttgcaccacc aggagcctca aatttttcaa taaattcacc tgactgcaca ttaggacttt    120
ggctttgagc ttcccacctc tcagttactt gctgaatact gtctgcttca tcaatattat    180
cataggtgtg cccaaatgat atttgcaacc cttccctgtt ggctacttgt ctcaccattg    240
taggcctaat gggagacgga tccgtagttt aacacattat acactagggt cgactgtgga    300
attgtgagcg ctcacaattc cacaacctag ggtcgactgt ggaattgtga gcgctcacaa    360
ttccacaacc tagggtcgac tgtggaattg tgagcgctca caattccaca acctagtaaa    420
ttttatattt accttagagc tttaaatctc tgtaggtagt ttgtcca               467

<210> SEQ ID NO 27
<211> LENGTH: 467
<212> TYPE: DNA
<213> ORGANISM: Artificial Sequence
<220> FEATURE:
<223> OTHER INFORMATION: Description of Artificial Sequence: DNA
      construct

<400> SEQUENCE: 27
agcttggaca aactacctac agagatttaa agctctaagg taaatataaa atttactagg      60
ttgtggaatt gtgagcgctc acaattccac agtcgaccct aggttgtgga attgtgagcg    120
ctcacaattc cacagtcgac cctaggttgt ggaattgtga gcgctcacaa ttccacagtc    180
gaccctagtg tataatgtgt taaactacgg atccgtctcc cattaggcct acaatggtga    240
gacaagtagc caacagggaa gggttgcaaa tatcatttgg gcacacctat gataatattg    300
atgaagcaga cagtattcag caagtaactg agaggtggga agctcaaagc caaagtccta    360
atgtgcagtc aggtgaattt attgaaaaat ttgaggctcc tggtggtgca aatcaaagaa    420
ctgctcctca gggatcctaa ttgtttgtgt attttagatt ccaacca                  467

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 28
tcgcgattcc cacgaatcaa atggc                                           25

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
tctggcacat acgatttagg t                                               21

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence: DNA
      construct

<400> SEQUENCE: 30
actcgagaag gcgcgcccaa ctcgctcgcc cgggccgaac cagttggcta gcgc           54

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: DNA
      construct

<400> SEQUENCE: 31
ggccgcgcta gccaactggt tcggcccggg cgagcgagtt gggcgcgcct tctcgagt       58